US008109990B2

(12) United States Patent
Paul et al.

(10) Patent No.: US 8,109,990 B2
(45) Date of Patent: Feb. 7, 2012

(54) LOW PROFILE SUPPORT FRAME AND RELATED INTRALUMINAL MEDICAL DEVICES

(75) Inventors: Ram H. Paul, Bloomington, IN (US); Sean D. Chambers, Bloomington, IN (US); Charles L. McIntosh, Silver Spring, MD (US); Charles W. Agnew, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 12/711,915

(22) Filed: Feb. 24, 2010

(65) Prior Publication Data

US 2010/0217381 A1  Aug. 26, 2010

Related U.S. Application Data

(60) Provisional application No. 61/154,856, filed on Feb. 24, 2009.

(51) Int. Cl.
*A61F 2/82* (2006.01)
(52) U.S. Cl. ...................... 623/1.15; 623/1.36
(58) Field of Classification Search ............... 623/1.15, 623/1.18, 1.2, 1.36, 2.11, 2.36
See application file for complete search history.

(56) References Cited

U.S. PATENT DOCUMENTS

| 4,494,531 A | 1/1985 | Gianturco |
| 4,832,055 A | 5/1989 | Palestrant |
| 4,994,077 A | 2/1991 | Dobben |
| 5,607,465 A | 3/1997 | Camilli |
| 6,200,336 B1 | 3/2001 | Pavcnik et al. |
| 6,623,506 B2 | 9/2003 | McGuckin, Jr. et al. |
| 7,128,759 B2 | 10/2006 | Osborne et al. |
| 7,303,571 B2 | 12/2007 | Makower et al. |
| 7,361,189 B2 | 4/2008 | Case et al. |
| 7,569,071 B2 | 8/2009 | Haverkost et al. |
| 2001/0039450 A1 | 11/2001 | Pavcnik et al. |
| 2005/0187614 A1 | 8/2005 | Agnew |
| 2006/0241675 A1 | 10/2006 | Johnson et al. |
| 2007/0112423 A1 | 5/2007 | Chu |
| 2008/0046071 A1 | 2/2008 | Pavcnik |
| 2008/0140110 A1 | 6/2008 | Spence |
| 2009/0234434 A1 | 9/2009 | Johnson et al. |

FOREIGN PATENT DOCUMENTS

WO   WO2009088957   7/2009

OTHER PUBLICATIONS

International Searching Authority, The International Search Report and Written Opinion of the International Searching Authority, May 20, 2010, for International Application No. PCT/US2010/025245.

*Primary Examiner* — Thomas J Sweet
*Assistant Examiner* — Matthew Schall
(74) *Attorney, Agent, or Firm* — Buchanan Nipper

(57) ABSTRACT

A low profile support frame for use as an or in an expandable intraluminal medical device includes first and second wire members that define arcuate paths having opposing curves. Connectors join the wire members, and barbs can be disposed on the connectors. The support frame has radially compressed and radially expanded configurations. When the support frame is in the radially expanded configuration, substantially no portion of the support frame is disposed on a first transverse axis of the frame opposite one end of the frame and substantially no portion of the frame is disposed on a second transverse axis of the frame opposite the other end of the frame. The support frame can be used as an intraluminal medical device by itself or as a component in a medical device that includes other components, such as a stent, prosthetic valve, occluder, or filter.

21 Claims, 10 Drawing Sheets

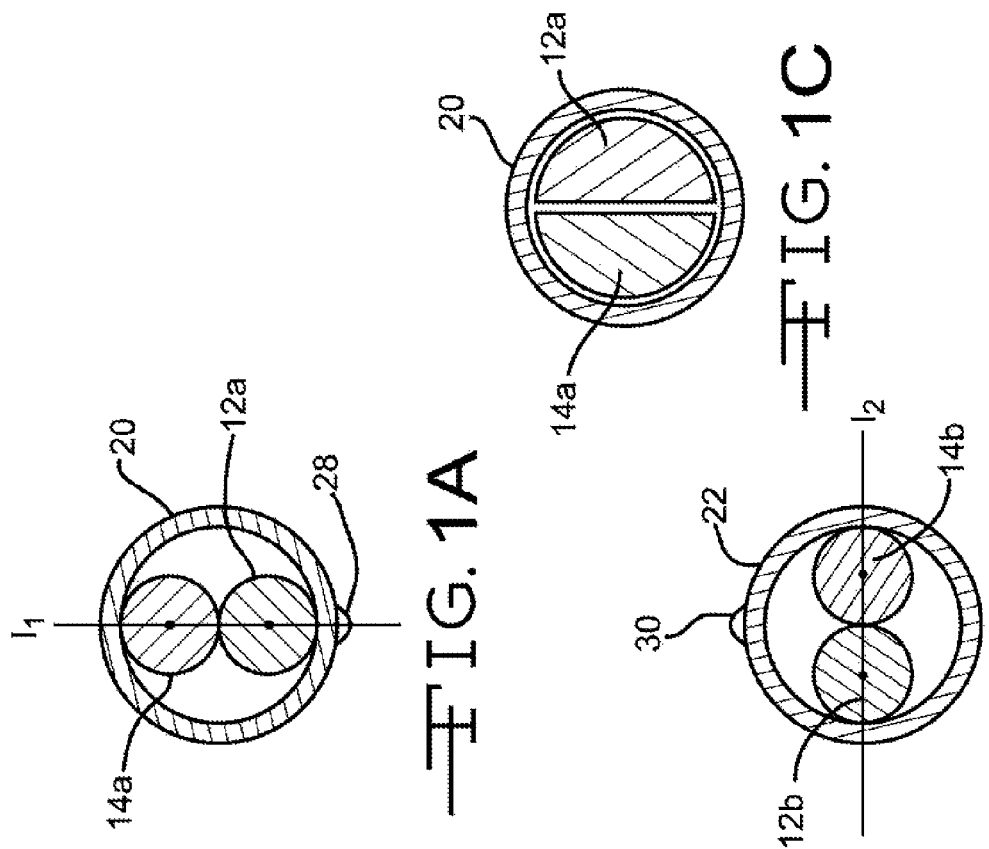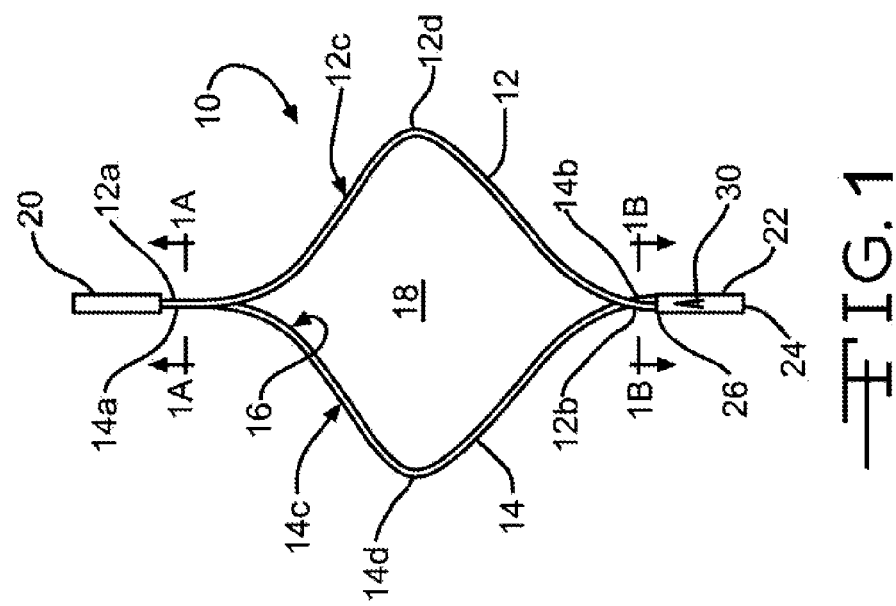

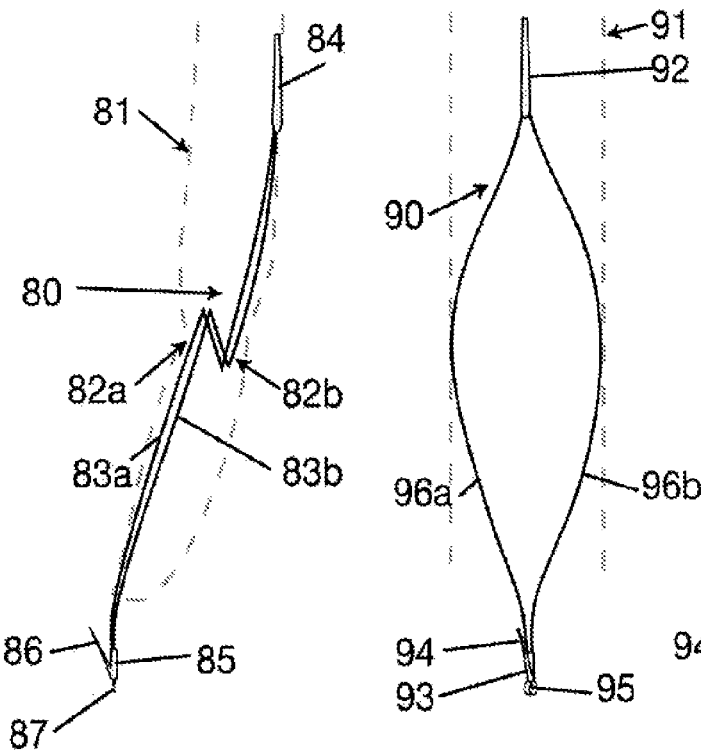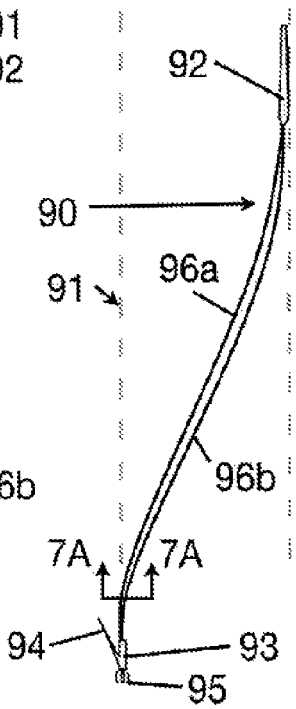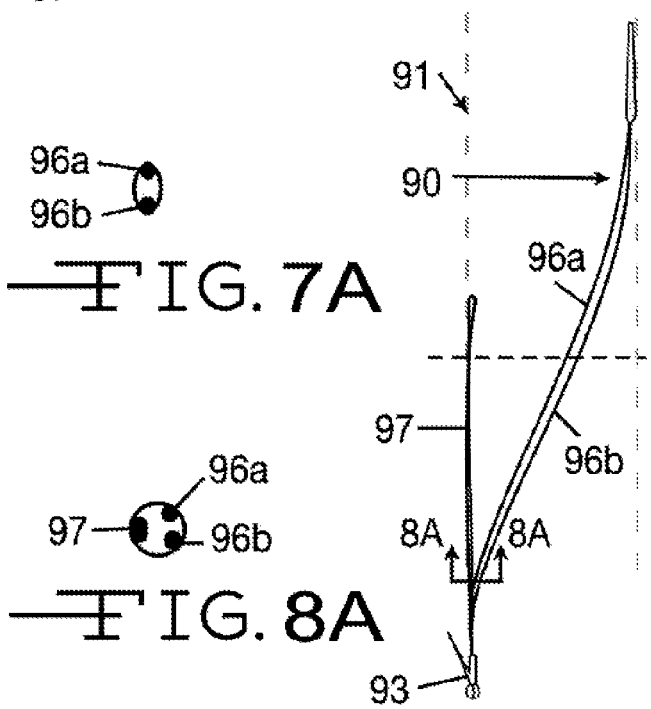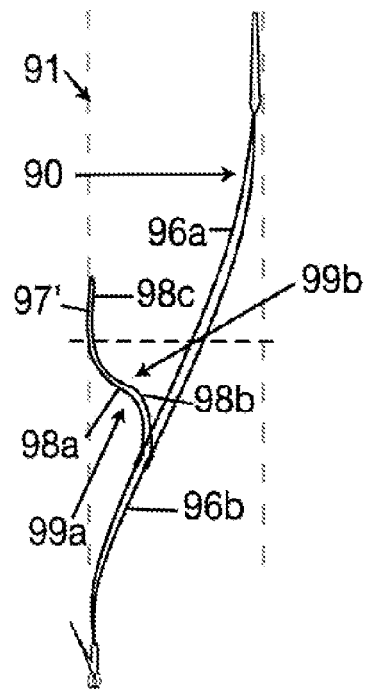

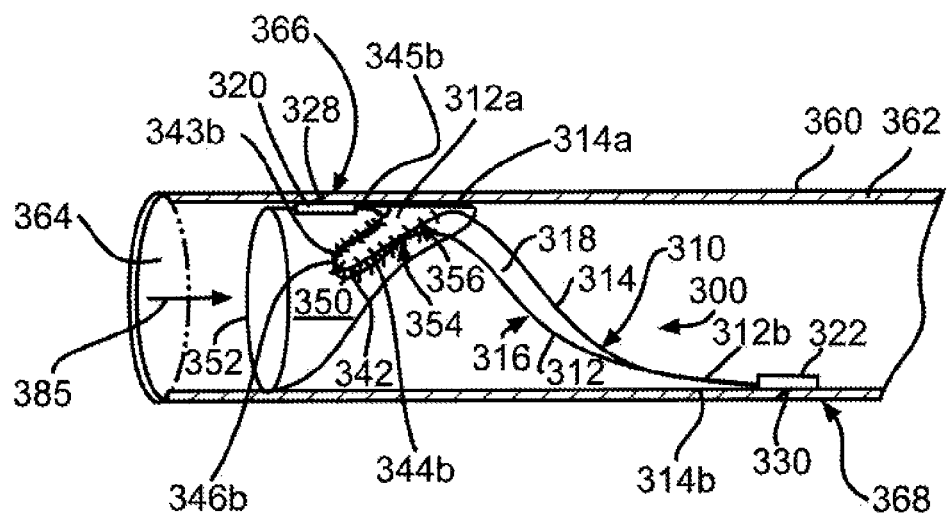
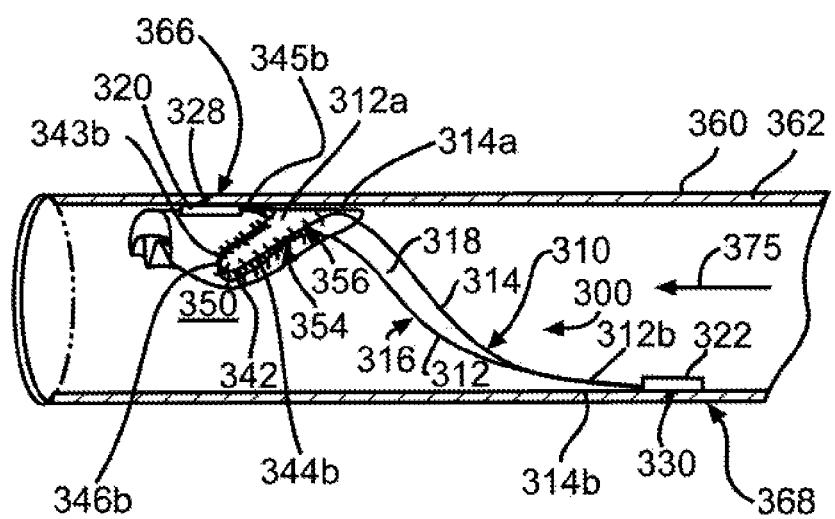

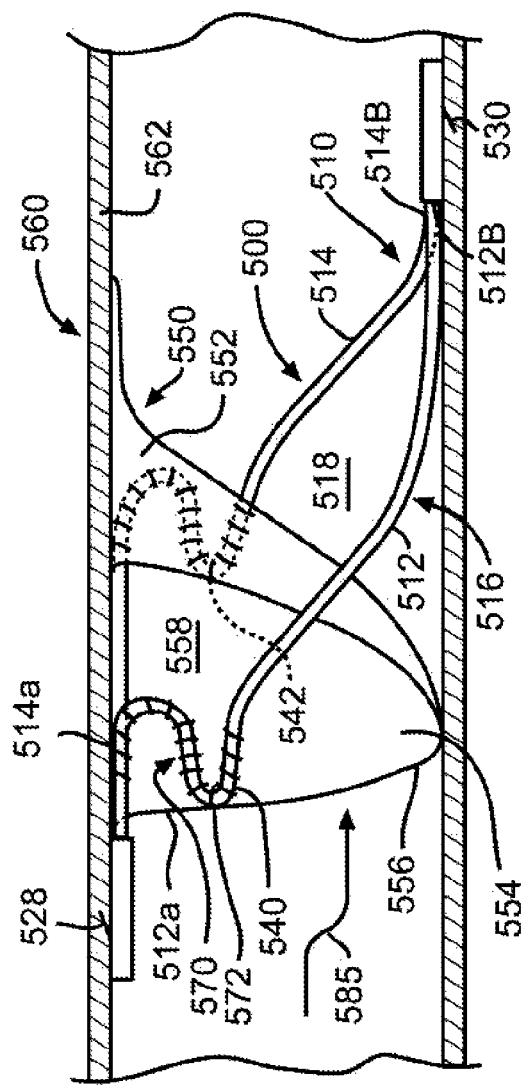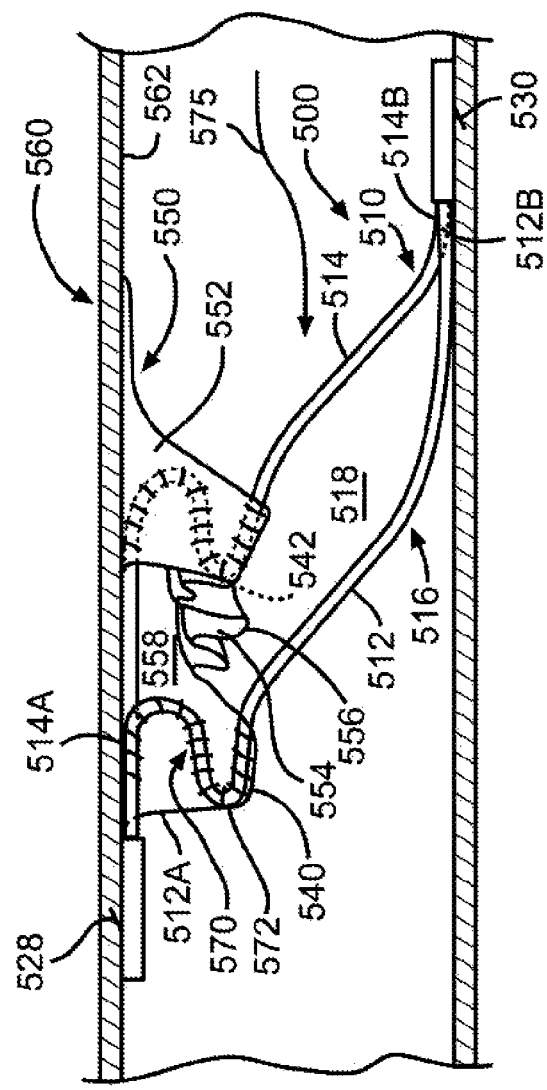

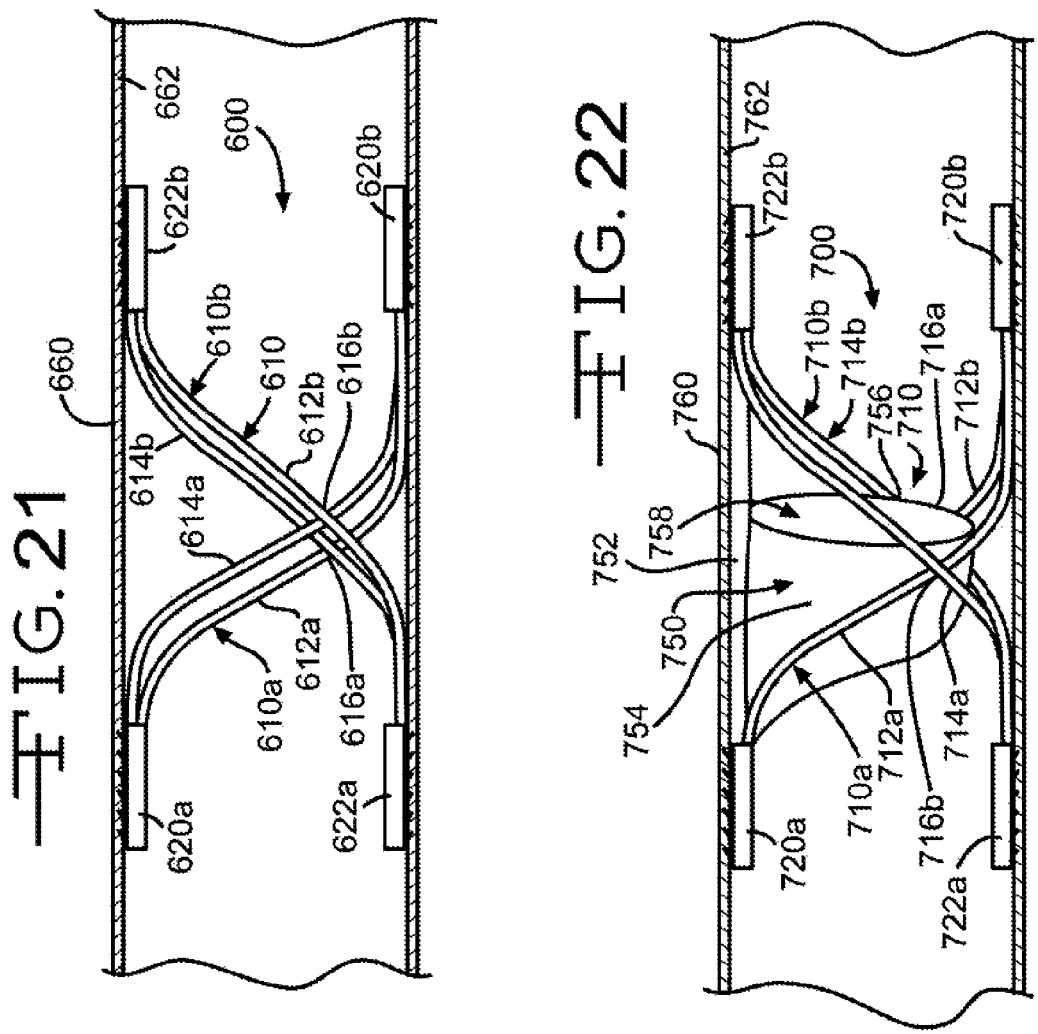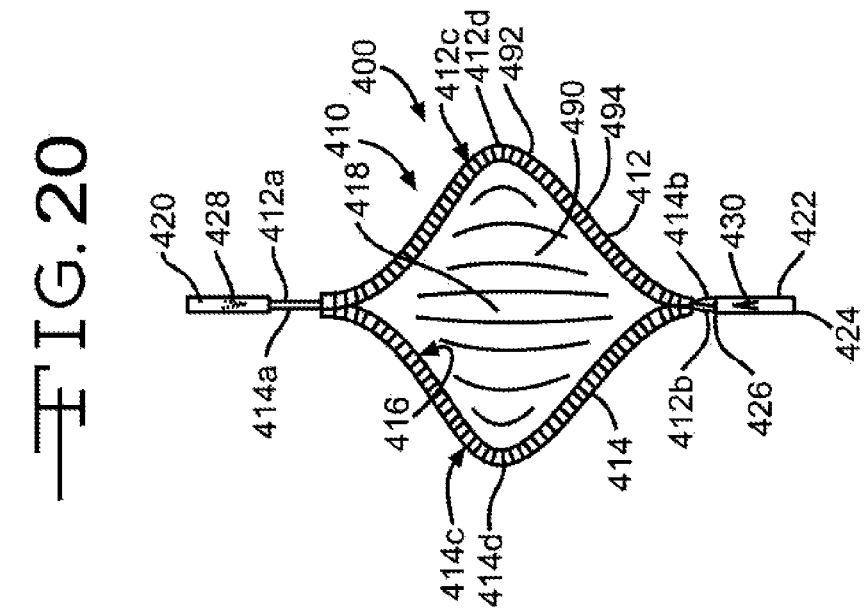

LOW PROFILE SUPPORT FRAME AND RELATED INTRALUMINAL MEDICAL DEVICES

CROSS REFERENCE TO RELATED APPLICATION

This application claims priority to U.S. Provisional Application Ser. No. 61/154,856, filed on Feb. 24, 2009. The entire contents of this provisional application are hereby incorporated by reference into this disclosure.

FIELD

The disclosure relates generally to the field of expandable intraluminal medical devices. Particular embodiments relate to low profile support frames for use in such medical devices. Additional embodiments relate to prosthetic valves, stents, filters, occluders, and other intraluminal medical devices that incorporate one or more low profile support frames.

BACKGROUND

A variety of expandable intraluminal medical devices have been developed over recent years. For example, stents are routinely used in several body lumens as a means for providing support to ailing vessels, such as coronary and non-coronary vessels. Occlusion devices are used to substantially block fluid flow through a body vessel, and prosthetic valves are used to regulate fluid flow through a body vessel. Both prosthetic heart valves and venous valves have been the subject of significant development efforts in recent years.

Expandable intraluminal medical devices are typically delivered to a point of treatment using a delivery system designed for percutaneous techniques. In a conventional procedure, a caregiver navigates the delivery system through one or more body vessels until the expandable intraluminal medical device, which is typically contained in a distal tip of the delivery system, is positioned at or near the desired point of treatment. Next, the caregiver deploys the expandable intraluminal medical device from the delivery system, either by removing a constraining force for self-expandable devices or by providing an expansive force for balloon-expandable devices. Once deployment is complete, the delivery system is removed from the body vessel, leaving the intraluminal medical device in an expanded configuration at the point of treatment. This delivery and deployment technique is largely conventional and is used for most types of expandable intraluminal medical devices, including stents, occluders, valves, and other types of devices.

During delivery, expandable intraluminal medical devices are maintained in a compressed or reduced-diameter configuration within the delivery system to ensure navigability of the delivery system through the body vessel. The navigability of the delivery system is directly related to its overall outer diameter. A relatively large diameter limits the ability of a delivery system to be navigated past curves, angles, side branch openings and other impediments, and also limits the ability of a delivery system to enter and/or be navigated through small diameter vessels.

Because the delivery system must carry the intraluminal medical device to the point of treatment in the body vessel, efforts to minimize the outer diameter of delivery systems are necessarily confined by the ability of the intraluminal medical device to be compressed. The material, construction, and configuration of the medical device can limit its ability to be compressed which, in turn, limits the useable outer diameter of the delivery system that will ultimately be used with the device.

Some intraluminal medical devices, including some prosthetic valves and occluders, include graft and/or valve members that add to the bulk of the support frame included in the device, compounding the difficulty associated with increasing the compressibility of the device. A need exists, therefore, for low profile support frames that can be used in one or more such expandable intraluminal medical devices, either independently of or in conjunction with other device components. Furthermore, a need exists for a variety of intraluminal medical devices that include a low profile support frame, including prosthetic valves, stents, filters, occluders, and the like.

BRIEF SUMMARY

Low profile support frames for use as or in expandable intraluminal medical devices are described. A low profile support frame according to an exemplary embodiment comprises a first wire member having first and second ends and defining a first arcuate path with a first curve disposed between the first and second ends; a second wire member having third and fourth ends and defining a second arcuate path with a second curve disposed between the third and fourth ends; a first connector attached to the first and third ends; and a second connector attached to the second and fourth ends. The first and second wire members form a closed circumference that defines a closed cell, and the first connector is spaced from the second connector along a longitudinal axis of the support frame.

In alternate embodiments, one or more of the first and second wire members comprises a series of curves that defines a path.

Expandable intraluminal medical devices that include a low profile support frame are also described. A prosthetic valve according to an exemplary embodiment comprises a support frame providing a closed circumference defining a closed cell. The support frame includes a first wire member having first and second ends and defining a first arcuate path with a first curve disposed between the first and second ends, a second wire member having third and fourth ends and defining a second arcuate path with a second curve disposed between the third and fourth ends, a first hollow connector disposed around the first and third ends, and a second hollow connector disposed around the second and fourth ends. A valve member having first and second edges is attached to the support frame with at least a portion of the first edge attached to the support frame and the second edge being substantially free of the support frame and adapted to move between first and second positions.

A prosthetic valve according to another exemplary embodiment comprises a first wire member having first and second ends and defining a first arcuate path with a first curve disposed between the first and second ends; a second wire member having third and fourth ends and defining a second arcuate path with a second curve disposed between the third and fourth ends; a first hollow connector disposed around the first and third ends such that the first end is disposed on top of the third end with respect to a plane containing the closed circumference; a second hollow connector disposed around the second and fourth ends such that the second and fourth ends are disposed substantially side-by-side with respect to the plane containing the closed circumference; and a valve member having first and second edges, at least a portion of the first edge attached to the support frame and the second edge being substantially free of the support frame and adapted to move between first and second positions.

Additional understanding of the low profile support frames and various intraluminal medical devices can be obtained with review of the following detailed description and the appended drawings.

BRIEF DESCRIPTION OF THE DRAWINGS

FIG. 1 is a perspective view of a first exemplary support frame.

FIG. 1A is a cross-sectional view of the support frame illustrated in FIG. 1, taken along line 1A-1A.

FIG. 1B is a cross-sectional view of the support frame illustrated in FIG. 1, taken along line 1B-1B.

FIG. 1C is a cross-sectional view of an alternative support frame.

FIG. 5 is a side view of an exemplary stent deployed in a common bile duct (illustrated in phantom).

FIG. 6 is a top view of a second exemplary stent deployed in a body vessel (illustrated in phantom).

FIG. 7 is a side view of the stent illustrated in FIG. 6.

FIG. 7A is a cross-sectional view of the stent illustrated in FIG. 6, taken along line 7A-7A.

FIG. 8 is a side view of a third exemplary stent deployed in a body vessel (illustrated in phantom).

FIG. 8A is a cross-sectional view of the stent illustrated in FIG. 8, taken along line 8A-8A.

FIG. 9 is a side view of a fourth exemplary stent deployed in a body vessel (illustrated in phantom).

FIG. 16 is a three-quarter view of a body vessel in which the prosthetic valve illustrated in FIG. 15 has been deployed. The valve is shown in a closed configuration.

FIG. 17 is a three-quarter view of a body vessel in which the prosthetic valve illustrated in FIG. 15 has been deployed. The valve is shown in an open configuration.

FIG. 18 is a three-quarters view of a body vessel in which an exemplary prosthetic valve has been deployed. The valve is shown in a closed configuration.

FIG. 19 is a three-quarters view of a body vessel in which an exemplary prosthetic valve has been disposed. The valve is shown in an open configuration.

FIG. 20 is a perspective view of an exemplary occluder.

FIG. 21 is a cross-sectional view of a body vessel in which an exemplary support frame has been deployed.

FIG. 22 is a cross-sectional view of a body vessel in which an exemplary prosthetic valve has been deployed. The valve is shown in a closed configuration.

DETAILED DESCRIPTION

Figure 2:
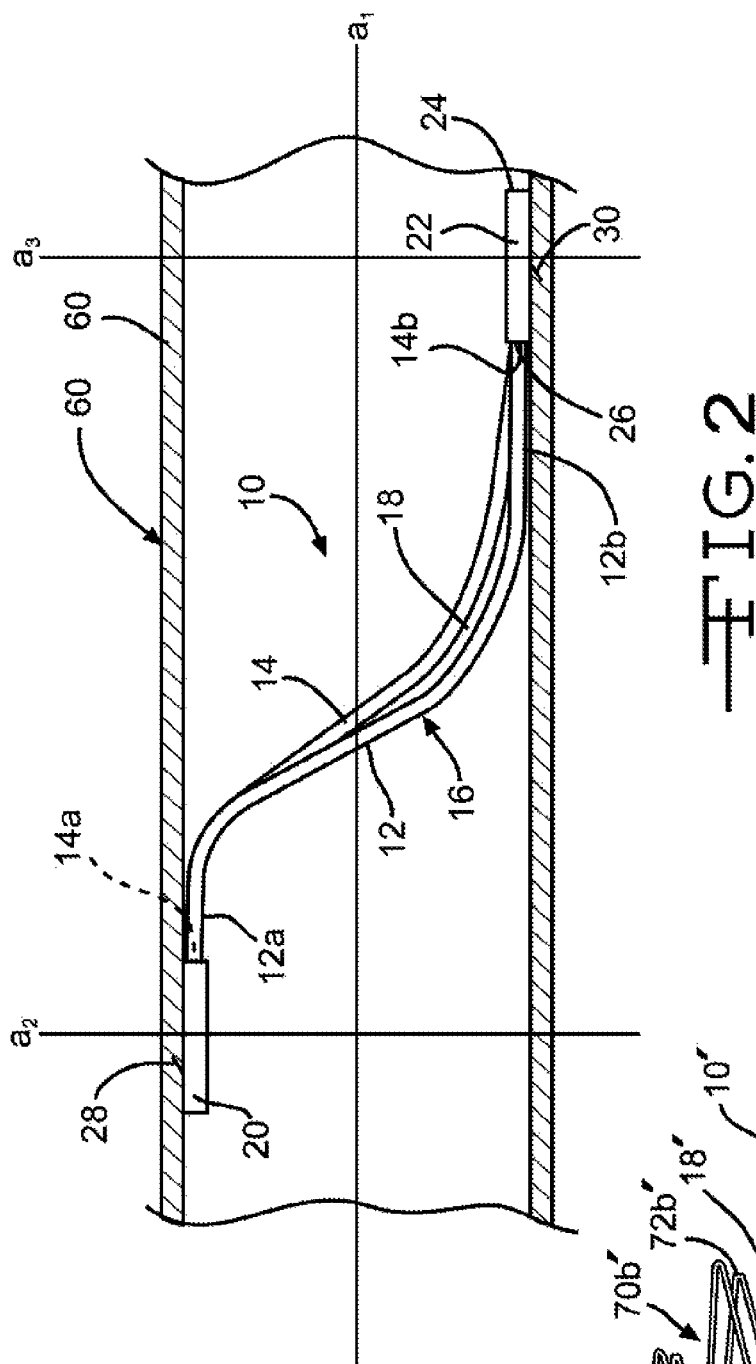
FIG. 2 is a partial sectional view of a body vessel in which the support frame illustrated in FIG. 1 has been deployed.

The following detailed description and appended drawings describe and illustrate various exemplary embodiments of the invention. The description and drawings serve to enable one skilled in the art to make and use the inventive apparatuses, and are not intended to limit the scope of the invention or the protection sought in any manner.

FIGS. 1, 1A and 1B illustrate an exemplary support frame 10. The support frame 10 includes first 12 and second 14 wire members. The first wire member 12 includes a first end 12a and a second end 12b. The wire member 12 defines an arcuate path 12c that includes a curve 12d disposed substantially at a midpoint between the first 12a and second 12b ends. Similarly, the second wire member 14 includes first 14a and second 14b ends and defines an arcuate path 14c that includes a curve 14d disposed substantially at a midpoint between the ends 14a, 14b.

The wire members 12, 14 cooperatively define a closed circumference 16 that, in turn, defines a single closed cell 18. A first connector 20 is disposed at one end of the support frame 10 and a second connector 22 is disposed at the opposite end of the support frame 10. The first ends 12a, 14a of the first 12 and second wire 14 members are disposed within the first connector 20, and the second ends 12b, 14b of the first 12 and second 14 wire members are disposed in the second connector 22. Each of the connectors 20, 22 is attached to the appropriate ends 12a, 12b, 14a, 14b to maintain the closed circumference 16 defined by the wire members 12, 14. While the connectors 20, 22 are illustrated as hollow members that receive the ends 12a, 12b, 14a, 14b of the wire members 12, 14, it is understood that any suitable means for connecting wire members together can be used, including mechanical connections, such as crimping, adhesives, a connection formed by annealing or brazing, or any other suitable structure that provides a means for connecting wire members. The specific structure selected for the means for connecting the wire members in a support frame according to a particular embodiment of the invention will depend on various considerations, including the materials used in the wire members 12, 14.

It is noted that, while the support frame 10 is illustrated as being formed of independent wire members connected to each other, the support frame 10 can be formed of a unitary piece of material using suitable techniques and materials. For example, the support frame could be cut from a tube of shape memory material using conventional or other suitable techniques. For example, the support frame could be cut from a tube of nitinol using laser cutting or other suitable techniques, followed by expansion and heat treatment steps that are known in the art. In these unitary embodiments, the wire members comprise struts in the resulting structure and the connectors 20, 22 comprise joints at which individual struts are joined to each other. Connectors that are separate and distinct from the struts are not necessary in these embodiments—the joints perform the connecting function of the connectors in these embodiments. Also, a single wire member could be used to form the support frame using suitable bending techniques. In these embodiments, bends in the wire member eliminate the need for connectors. It is noted, though, that in these embodiments, the inclusion of one or more connectors might still be considered advantageous as a crimping force providing by the connector may maintain a bend in the single wire member in a minimal thickness. It is also noted that a single wire member having one end formed by a bend and the other end formed by attaching two independent ends of the single wire member can be used to form the support frame.

While the illustrated support frame 10 includes two wire members 12, 14, it is expressly understood that support frames can include any suitable number of wire members. It is noted, though, the inclusion of only two wire members is considered particularly advantageous at least because two wire members, either as separate wire members, struts in a unitary structure, or as a unitary wire formed into a support frame, is believed to provide the minimum structure needed to achieve the beneficial results described herein, such as the minimal nature of the overall bulk of the support frame.

In the illustrated embodiment, each connector 20, 22 includes a closed 24 and an open 26 end. The open end 26 is sized and configured to receive the appropriate ends 12a, 12b, 14a, 14b. The closed end 24 does not provide access to the inside of the connector 20, 22. A barb is advantageously included on each of the connectors 20, 22. In this embodiment, the barb 28 on the first connector 20 is disposed on a surface of the first connector 20 that faces in a substantially opposite direction than the direction faced by the surface of the second connector 22 on which barb 30 is disposed, relative to a plane containing the closed circumference 16 defined by the wire members 12, 14. Also in this embodiment, the first barb 28 extends away from the first connector 20 in a direction that is different from the direction in which the second barb 30 extends away from the second connector 22. As illustrated in the figure, the barbs 28, 30 advantageously extend in substantially opposite directions. This configuration is expected to provide advantageous anchoring characteristics. It is noted that the barbs 28, 30 are not necessarily drawn to scale relative to any other component and/or element of the frame 10, and are shown as relatively large elements for illustrative purposes only.

As best illustrated in FIGS. 1A and 1B, pairs of the ends 12a, 12b, 14a, 14b are advantageously positioned in their respective connectors 20, 22 such that an imaginary line $I_1$ containing the geometric centers (illustrated by dots) of ends 12a, 14a orients substantially orthogonally to an imaginary line $I_2$ containing the geometric centers (illustrated by dots) of ends 12b, 14b. Thus, when the frame 10 is substantially flattened into a plane, as illustrated in FIG. 1, the first ends 12a, 14a are disposed with one end 14a substantially on top of the other 12a, relative to a plane containing the closed circumference 16 defined by the wire members 12, 14. The second ends 12b, 14b are disposed substantially side-by-side, relative to a plane containing the closed circumference 16 defined by the wire members 12, 14. Thus, a plane containing the geometric centers of ends 12a, 14a is disposed substantially orthogonal to a plane containing the geometric centers of ends 12b, 14b. This configuration of the ends 12a, 12b, 14a, 14b is considered advantageous at least because it aids in maintaining a desirable configuration of the closed cell 18 defined by the closed circumference 16 following deployment of the support frame 10 in a body vessel.

FIG. 1C illustrates an alternate arrangement for the first pair of ends 12a, 14a. In this embodiment, the ends 12a, 14a define complimentary semi-circular structures. This configuration minimizes the space needed within the connector 20 to contain the ends 12a, 14a, further reducing the overall bulk of the support frame. This structure also eliminates or reduces the need to fill voids within the connector 20 (visible in FIG. 1A) with filler material, such as solder or other material. Indeed, this structure can facilitate the use of purely mechanical means for attaching the connector 20 to the ends 12a, 14a, such as crimped connectors. In this embodiment, the entire wire members can define the complimentary shapes illustrated in FIG. 1C, or just the ends 12a, 14a or another longitudinal portion of the wire members can define the complimentary shapes, with the remainder of the wire members having a round or other cross-section shape. Also, while FIG. 1C only illustrates one pair of ends 12a, 14a, it is understood that one or both pairs of ends can define complimentary shapes. Furthermore, one pair of ends can define complimentary shapes, such as illustrated in FIG. 1C, while the other pair of ends has a different structure, such as illustrated in FIG. 1A or 1B. Lastly, it is understood that, while FIG. 1C illustrates semi-circular complimentary shapes, it is understood that any suitable set of complimentary shapes can be used, including other mating shapes, interlocking shapes, and any other suitable shapes.

The frame 10 can be modified to include a structural member, such as one or more of a ball, ring, hook, loop, or other suitable structural member that facilitates repositioning and/or retrieval of the frame within or from a body vessel using an appropriate catheter or other suitable device adapted to engage the structural member. The structural member can be integrally formed with the frame 10 or one or both connectors 20, 22 or can comprise a separately attached member. Furthermore, the structural member can be positioned on the frame 10 at any suitable location. In one exemplary embodiment, a loop is formed on one connector opposite the open cell defined by the wire members. A retrieval device with a hook can then be used to engage the loop to facilitate repositioning and/or retrieval of the device.

FIG. 2 illustrates the support frame 10 disposed within a lumen 64 of a body vessel 60. The low profile nature of the support frame 10 can be seen immediately from this view. Upon deployment, the frame 10 adopts an expanded configuration in which the first pair of ends 12a, 14a is spaced from the second pair of ends 12b, 14b on a lengthwise axis $a_1$ of the frame 10. The first pair of ends 12a, 14a extends in a first direction away from a structural midpoint of the support frame 10 along the lengthwise axis a1, while the second pair of ends 12b, 14b extends in a second, substantially opposite direction away from the structural midpoint of the support frame 10 along the lengthwise axis $a_1$. The first pair of ends 12a, 14a extends along an axis that is different from, but substantially parallel to, the lengthwise axis $a_1$ and the second pair of ends 12b, 14b extends along an axis that is different from, but substantially parallel to, both the lengthwise axis $a_1$ and the lengthwise axis of the first pair of ends 12a, 14a. Also, no portion of the support frame 10 is disposed on a transverse axis $a_2$ opposite the first pair of ends 12a, 14a and/or the first connector 20, and no portion of the support frame 10 is disposed on a transverse axis $a_3$ opposite the second pair of ends 12b, 14b and/or the second connector 22. When deployed in a body vessel, as illustrated in FIG. 2, the wire members 12, 14, and the arcuate paths 12c, 14c defined by the members 12, 14, are in substantially continuous contact with the inner surface of the wall 62 of the body vessel 60. The first connector 20 and first pair of ends 12a, 14a is in contact with a portion of the wall 62 of the body vessel 60 that is substantially opposite the portion of the wall 62 with which the second connector 22 and the second pair of ends 12b, 14b is in contact.

As best illustrated in FIG. 2, the arcuate paths 12c, 14c and curves 12d, 14d defined by the wire members 12, 14 position the connectors 20, 22 and ends 12a, 14a, 12b, 14b in this manner upon adoption of an expanded configuration and allow the support frame 10 to exert a desirable force on the body vessel 60, such as an outwardly-directed radial force, despite the minimal nature of the structure of the support frame 10. The structure of the arcuate paths 12c, 14c and/or the curves 12d, 14d, including the radius of curvature for the various portions of the wire members 12, 14, can be varied and indeed optimized for particular support frames intended for particular uses. For example, the illustrated support frame 10 may be suitable for use as a stent, as described below. An alternative support frame that positions the central portion of the arcuate path 12c, 14c on a substantially transverse axis to the lengthwise axis a1 of the support frame 10, upon expansion, is believed to be particularly advantageous for use in an occluder medical device that includes such a support frame. A skilled artisan will be able to determine an appropriate structure of the arcuate paths and/or curves for a support frame according to a particular embodiment based on various considerations, including the nature of the body vessel in which the support frame is intended to be deployed, the nature of fluid flow through the body vessel, and the nature and function of any additional components included in a medical device that includes the support frame.

The wire members 12, 14 can be formed of any suitable resilient material acceptable for use in implantable medical devices. Examples of suitable materials include, but are not limited to, stainless steel, nitinol, nickel-cobalt-chromium alloys, nickel-cobalt-chromium-molybdenum alloys, polymeric materials, and other biocompatible materials. Nickel-cobalt-chromium-molybdenum alloys, such as MP35N (Carpenter Technology, Wyomissing, Pa.; MP35N is a registered trademark of SPS Technologies, Inc.), are considered particularly advantageous at least because of the relatively high tensile strength provided by these materials. As used herein, the term "wire member" does not refer to any particular size, diameter, or cross-sectional shape. While wire members having substantially circular cross-sectional shapes offer particular advantages, they are not required. Examples of other suitable cross-sectional shapes include, but are not limited to, flat, square, triangular, D-shaped, trapezoidal, and delta-shaped cross-sectional shapes. Also, as mentioned above, the support frame 10 can comprise a unitary member cut from an appropriate material, such as from a tube of shape memory material. In these embodiments, the wire members comprise struts in the structure resulting from the cutting process.

The connectors 20, 22 can be formed from the same material or a different material than that of the wire members 12, 14. Skilled artisans will be able to select appropriate materials for use in a support frame 10 according to a particular embodiment of the invention based on various considerations, including the intended use, treatment environment and manufacturing demands of the support frame 10. The inventors have determined that wire members 12, 14 formed of nitinol and connectors 20, 22 formed of stainless steel provide a support frame with desirable characteristics for use in a variety of applications, including as a component in intraluminal medical devices, such as stents, prosthetic valves, and occluders.

Figure 3:
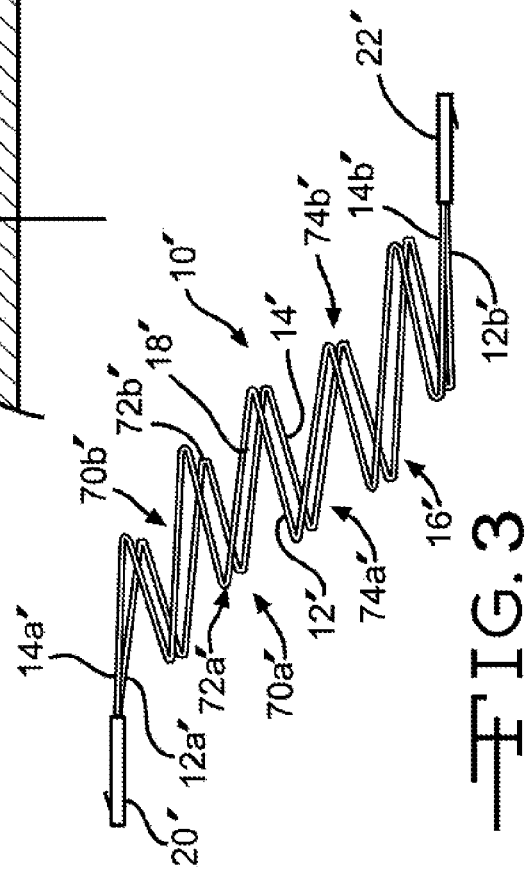
FIG. 3 is a perspective view of a second exemplary support frame.

FIG. 3 illustrates a support frame 10' according to an alternative embodiment. The frame 10' is similar to the frame 10 illustrated in FIG. 1, except as detailed below. Thus, the frame 10' includes first 12' and second 14' wire members. The first wire member 12' includes a first end 12a' and a second end 12b', and the second wire member 14' includes a first end 14a' and a second end 14b'. The wire members 12', 14' cooperatively define a closed circumference 16' that, in turn, defines a single closed cell 18'. A first connector 20' is disposed at one end of the support frame 10' and a second connector 22' is disposed at the opposite end of the support frame 10'. The first ends 12a', 14a' of the first 12' and second wire 14' members are disposed within the first connector 20', and the second ends 12b', 14b' of the first 12' and second 14' wire members are disposed in the second connector 22'. Each of the connectors 20', 22' is attached to the appropriate ends 12a', 12b', 14a', 14b' to maintain the closed circumference 16' defined by the wire member 12', 14'.

In this embodiment, the first wire member 12' comprises a first series 70a' of curves 72a' that define a first serpentine path 74a', and the second wire member 14' comprises a second series 70b' of curves 72b' that define a second serpentine path 74b'. While the frame 10' is illustrated with both wire members 12', 14' defining serpentine paths, it is understood that a frame can be constructed with only one of the wire members defining a serpentine path without departing from the scope of the invention. In these alternative embodiments, the wire member not defining a serpentine path can have any suitable configuration, including an arcuate path as described and illustrated in regards to the embodiment illustrated in FIG. 1.

The inclusion of a series of curves that define a serpentine path is considered advantageous at least because this configuration is expected to increase the radial expandability and stability of the support frame 10'.

Figures 4, 10:
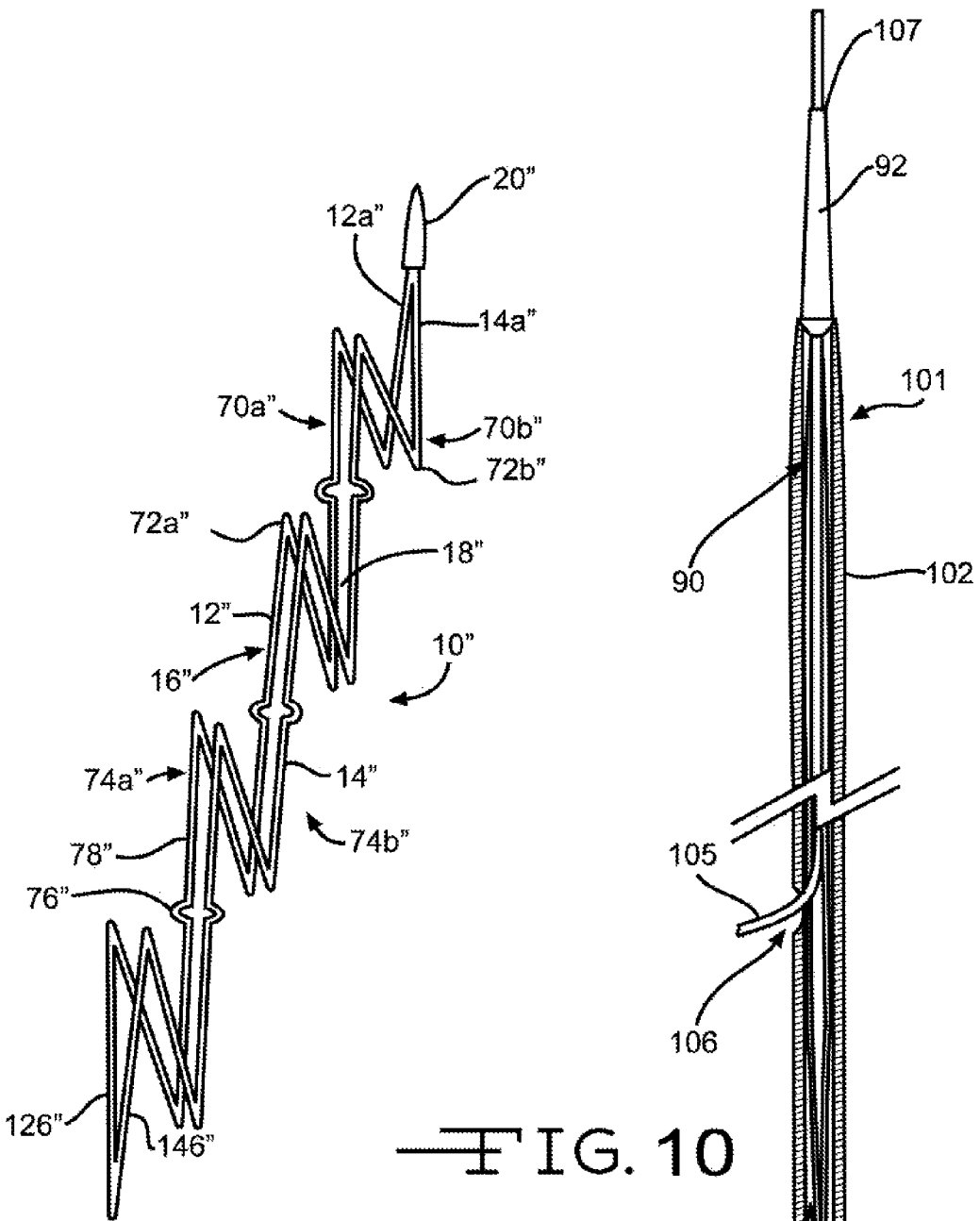
FIG. 4 is a perspective view of a third exemplary support frame.
FIG. 10 is a partial sectional view of a delivery system containing an exemplary stent.

FIG. 4 illustrates a support frame 10" according to another alternative embodiment. The frame 10" is similar to the frame 10 illustrated in FIG. 1, except as detailed below. Thus, the frame 10" includes first 12" and second 14" wire members. The first wire member 12" includes a first end 12a" and a second end 12b", and the second wire member 14" includes a first end 14a" and a second end 14b". The wire members 12", 14" cooperatively define a closed circumference 16" that, in turn, defines a single closed cell 18". A first connector 20" is disposed at one end of the support frame 10". The first ends 12a", 14a" of the first 12" and second wire 14" members are disposed within the first connector 20".

In this embodiment, the first wire member 12" comprises a first series 70a" of curves 72a" that define a first serpentine path 74a", and the second wire member 14" comprises a second series 70b" of curves 72b" that define a second serpentine path 74b". Each of the wire members 12", 14" also includes one or more curves 76" disposed along the length on an interconnecting section 78" between curves 72a", 72b" of the series 70a", 70b" of curves. The curves 76" can comprise curvilinear curves, as illustrated, angulated, or other curves, but do not comprise curves that substantially alter the path of the interconnecting section 78". The inclusion of such curves is considered advantageous at least because they provide a flexing zone to the interconnecting sections 78" that allow the frame 10" to better conform to a tortuous duct or vessel. The inclusion of curves 76" is also expected to facilitate deployment of the frame 10", or an intraluminal medical device including the frame 10", from side-viewing endoscopes, which have an acute delivery angle.

While the support frames described herein are considered useful independent of additional components, as an intraluminal stent, for example, the frames are also useful as a platform onto which other components and or functionalities can be added to provide new and useful intraluminal medical devices of various types, such as stents, prosthetic valves, occluders, filters, and the like. Various examples of such devices are described below.

The inventive support frames can be used as a component in a removeable biliary stent. Current plastic biliary stents last only about six months before becoming clogged and requiring removal and/or replacement. Thus, there is a need for a stent that is less likely to become clogged. The low profile nature of the inventive support frames make them well-suited for this application. In these embodiments, the wire members of the frame advantageously can be coated and/or encased in a polymer, such as Thoralon or another suitable polymer, to prevent cells/tissue from growing over the wire members, which could hinder retrieval and/or removal of the stent. Alternatively, the stent could be used as a short term measure to dilate the duct to allow passage or removal of a larger stone or calculi such that the polymer wouldn't be necessary. The stent could even be used to capture the stone and retain it while being removed from the duct, thereby removing the stone. In placing these stents in the common bile duct (or pancreatic duct), the proximal pair of ends of the support frame would extend from the Papilla of Vater into the duct, allowing the stent to be retrieved and removed under endoscopic viewing. These stents can be delivered from a sheath or directly from the accessory channel of a duodenoscope if it is placed close enough to the papilla to limit expansion until the stent was deployed within the duct. Trigger wires or constraining sutures can be used to control expansion during deployment. The connector joining the ends of the support frame wire members that is inserted into the duct may be shaped to aid in cannulation of the papilla, or it may include a passageway to allow the stent to be introduced into the duct over a wire guide used for the cannulation of the papilla.

It is noted that, while the support frames are described as being useful in stents intended for placement in certain bodily ducts and vessels, such as the common biliary duct and other ducts of the biliary tract, the frames, and indeed the devices that include the frames, can be used in any suitable bodily duct, passage, vessel or other location in need of a benefit provided by the support frame or medical device, such as a stenting function, a valving function, an occlusion function, or any other benefit provided by the support frame or medical device as appropriate. For example, the stents described herein could be adapted for use as urethral stents without departing from the scope of the invention. Also, the prosthetic valves described herein could be adapted for use as prosthetic venous valves and prosthetic heart valves without departing from the scope of the invention.

FIG. 5 illustrates an exemplary stent 80 positioned within a common bile duct 81 of an animal, such as a human. The stent 80 is similar to support frame 10 illustrated in FIG. 1, but includes first 82a and second 82b serpentine sections formed by bends in each of the wire members 83a, 83b. The first connector 84 is an elongate structure defining a tapered atraumatic tip which adapts the connector 84 for cannulation of the papilla during deployment of the biliary stent 80. The second connector 85 includes an outwardly-extending flap 86 that engages the major papilla during placement, which prevents the stent 80 from being completely inserted into the common bile duct 81 during placement and aids in retrieval of the stent 80. A loop 87 extends from the proximal end of the second connector 85, providing a structure that can be engaged by a suitable catheter-based or other tool for retrieval of the stent 80 from the duct 81.

As illustrated in the figure, the serpentine sections 82a, 82b can be positioned in contact with the duct wall across a stricture 88 therein. This positioning is considered advantageous because it is believed that the increased radial strength in the region of the stent 80 that includes the serpentine sections 82a, 82b will aid in maintaining the patency of the duct 81 at the stricture. It is noted that while the serpentine sections 82a, 82b are illustrated as being positioned substantially in the longitudinal middle of the stent 80, they can be positioned at any point along the length of the stent 80. Indeed, the serpentine sections 82a, 82b can be positioned in a custom location on a stent 80 that is based on a known or expected location of a specific stricture within a specific duct of a specific animal. Furthermore, while two serpentine sections 82a, 82b are illustrated, it is noted that any suitable number of serpentine sections can be included, including a series of serpentine sections such as illustrated in FIGS. 3 and 4. Also, each wire member can include any suitable number of serpentine sections, including zero, and the wire members need not have the same number of serpentine sections.

FIGS. 6, 7 and 7A illustrate another exemplary stent 90 positioned within a body vessel 91 of an animal, such as a human. Stent 90 is similar to the stent 80 illustrated in FIG. 5, except that the wire members do not include serpentine sections. Thus, the stent 90 includes a first connector 92 that is an elongate structure defining a tapered atraumatic tip and a second connector 93 that includes an outwardly-extending flap 94. In this embodiment, multiple loops 95 extend from the proximal end of the second connector 93, providing multiple structures that can be engaged by a suitable retrieval tool. The inclusion of multiple loops is considered advantageous because multiple loops provide multiple structures that can be engaged during retrieval, which is expected to increase the ease with which the stent 90 can be retrieved from the vessel 91.

FIG. 7A illustrates the spacing of the wire members 96a, 96b near the second connector 93.

FIGS. 8 and 8A illustrate an alternative structure for stent 90. In this embodiment, the stent 90 includes a stabilizing member 96 that extends along an axis that is substantially parallel to a lengthwise axis of the stent 90. A proximal end of the stabilizing member 97 is contained within the second connector 93 along with the ends of the wire members 96a, 96b, and a distal end of the stabilizing member 96 is free of contact with other portions of the stent 90. As illustrated in the figure, the stabilizing member 97 provides a structural member that extends along the wall of the duct 91, providing additional contact area between the stent 90 and the wall. It is believed that this additional contact area will enhance the ability of the stent 90 to maintain patency of the duct 91.

Comparing FIGS. 7A and 8A reveals a benefit of a stabilizing member that extends to the second connector 93. As illustrated in FIG. 8A, a stabilizing member 97 positioned in this manner provides a third point of support to aid in maintaining patency of the duct or body vessel near the second connector 93 and proximal end of the support frame. In biliary stent embodiments, this portion of the support frame is typically positioned near the sphincter of Odii, which controls the flow of digestive juices out of the biliary tract. The inclusion of a stabilizing member positioned in this manner in a biliary stent embodiment therefore, provides a third point of contact with the sphincter and is expected to enhance drainage of the duct following placement of the stent, which may reduce the likelihood that the stent will become clogged and/ or lengthen the time it takes for the stent to become clogged.

Any suitable structure can be used for the stabilizing member 97, including a single wire member, a looped wired member (as illustrated in FIGS. 8 and 8A), and any other suitable structure. A looped member is considered advantageous at least because the loop can be formed to include a rounded edge, which will be less likely to engage and/or pierce the duct wall than a simple blunt end of a single wire member. Furthermore, the distal end of the stabilizing member 96, no matter the structure used, can be coated or embedded within a material, such as a plastic or gel, that provides a desired atraumatic tip for the distal end.

FIG. 9 illustrates an alternative stabilizing member 97'. In this embodiment, the stabilizing member is connected to the wire members 96a, 96b at a point between the first 92 and second 93 connectors. A simple cannula or other suitable connection can be used to form this connection, or the stabilizing member 97' can be integrally formed with the wire members 96a, 96b. In this embodiment, the stabilizing member 97' is a loop structure that includes first 98a and second 98b bends that, in conjunction with the distal loop 98c, define first 99a and second 99b s-curves. This structure is expected to provide desirable radial strength characteristics while not adding significantly to the overall bulk of the stent 90.

It is noted that, while the illustrated biliary stents include a flap structure for engaging the papilla during placement, any suitable retention structure that mechanically prevents the biliary stent from being completely advanced into the biliary duct can be used, including multiple flaps, pigtails, balloons, and the like. It is also noted that, if prevention of migration at the opposite end of the stent is desired, one or more suitable retention structures can be placed on the distal end of the stent as well, either in addition to or in place of the flap or other retention structure positioned at the proximal end of the stent.

FIG. 10 illustrates the stent 90 of FIGS. 6 and 7 placed within a delivery system 101. The stent 90 is in a compressed configuration and circumferentially surrounded by a sheath 102. The loop 95 is engaged with a corresponding loop 103 on an inner member 104 of the delivery system 101. A guidewire 105 passes through exchange port 106 and through a passageway 107 defined by the first connector 92, allowing the stent 90 to be placed using guidewire-based delivery and deployment procedures. It is noted that, while the illustrated delivery system 101 is adapted for rapid-exchange or short wire applications, a convention over-the-wire delivery system could also be used. In these embodiments, the second connector 93 can also define a passageway through which the guidewire can pass.

FIGS. 11, 12, 12A, 13, and 13A illustrate a prosthetic valve device 100 according to an exemplary embodiment of the invention. The prosthetic valve device 100 includes a support frame 110 and an attached valve member 150. In each of the figures, the valve device is disposed within a body vessel 160. The body vessel 160 has a wall 162 and defines a lumen 164.

The support frame 110 is similar to the support frame 10 illustrated in FIG. 1 and described above. Thus, the support frame 110 includes first 112 and second 114 wire members. The first wire member 112 includes a first end 112a and a second end 112b. The wire member 112 defines an arcuate path 112c that includes a curve 112d disposed substantially at a midpoint between the first 112a and second 112b ends. Similarly, the second wire member 114 includes first 114a and second 114b ends and defines an arcuate path 114c that includes a curve disposed substantially at a midpoint between the ends 114a, 114b. The wire members 112, 114 cooperatively define a closed circumference 116 that, in turn, defines a single closed cell 118. A first connector 120 is disposed at one end of the support frame 110 and a second connector 122 is disposed at the opposite end of the support frame 110. The first ends 112a, 114a of the first 112 and second 114 wire members are disposed within the first connector 120, and the second ends 112b, 114b of the first 112 and second 114 wire members are disposed in the second connector 122.

Each of the connectors 120, 122 is attached to the appropriate ends 112a, 112b, 114a, 114b and includes a closed 124 and an open 126 end. Pairs of the ends 112a, 112b, 114a, 114b are disposed in the open end 126 of the appropriate connector 120, 124. A first barb (not illustrated in FIG. 11) is disposed on the first connector 120 and a second barb 130 on the second connector 122, substantially opposite to the first barb. It is noted that the barbs are not necessarily drawn to scale relative to any other component and/or element of the frame 110, and are shown as relatively large elements for illustrative purposes only.

The valve member 150 comprises a section of material, such as a sheet, that is attached to the support frame 110. The valve member 150 can be formed of any suitable material, and need only be biocompatible or be able to be rendered biocompatible. The material can advantageously be formed of a flexible material. Examples of suitable materials for the valve member 150 include natural materials, synthetic materials, and combinations of natural and synthetic materials. Examples of suitable natural materials include extracellular matrix (ECM) materials, such as small intestine submucosa (SIS), other bioremodellable materials, and fixed natural tissues, such as fixed bovine pericardium. Other examples of ECM materials that can be used in the prosthetic valves of the invention include stomach submucosa, liver basement membrane, urinary bladder submucosa, tissue mucosa, and dura mater. Tissue valves and portions thereof, such as a leaflet, patch, or other suitable portion of a tissue valve, can also be used. One or more sections of dermis, such as porcine and cadaveric dermis, can also be used as the valve member. ECM materials are particularly well-suited materials for use in the valve member 150, at least because of their abilities to remodel and become incorporated into adjacent tissues. These materials can provide a scaffold onto which cellular in-growth can occur, eventually allowing the material to remodel into a structure of host cells. Examples of suitable synthetic materials include polymeric materials, such as expanded polytetrafluoroethylene and polyurethane. The use of synthetic materials also allows the valve member to be formed as a web spanning appropriate portions of the support frame 110, such as by spraying, dipping or other suitable techniques for forming a webbing between structural members.

The valve member 150 includes a free edge 152 that is not attached to the support frame 110 and at least one portion 154 that is attached to the support frame by in any suitable manner, such as sutures 156. Alternatively, the valve member 150 can be attached to the support frame 110 by other means for attaching, such as adhesives, a heat seal, a tissue weld joint, a weave, or any other suitable means for attaching a valve member to a portion of a support frame. The specific means for attaching chosen will depend at least upon the materials used in the valve member 150 and the support frame 110, and a skilled artisan will be able to determine appropriate structure for a valve device according to a particular embodiment of the invention.

Alternatively, the one or both of the wire members 112, 114 can be passed into and/or through one or more portions of the valve member 150 to create an attachment between the support frame 110 and valve member 150. For example, one or both of the wire members 112, 114 can be inserted into a thickness of a portion of the valve member 150, such as an associated patch of tissue, extended along a length thereof and eventually passed back out of the thickness. This "tunneling through" a portion of the valve member may provide an attachment that eliminates the need for sutures or other attachment members, and is considered suitable for use in valve devices having valve members that provide an acceptable thickness that is able to accommodate the wire members 112, 114. Skilled artisans will be able to determine if this alternative attachment is suitable for any given valve member based on various considerations, including the thickness of the material of the valve member and the diameter or other relevant dimension of the wire members 112, 114. Valve members comprising fixed natural tissue are considered suitable for this approach. If this approach is used, the wire members 112, 114 can be passed into and through a portion of the valve member and subsequently connected together by applying one of the connectors 120, 124 to the wire members 112, 114. Also, the portion of the wire members 112, 114 that is expected to remain within the thickness of the valve member 150 can include structural adaptations that enhance the attachment between the support frame 110 and the valve member 150, such as microbarbs as described elsewhere herein.

Figure 11:
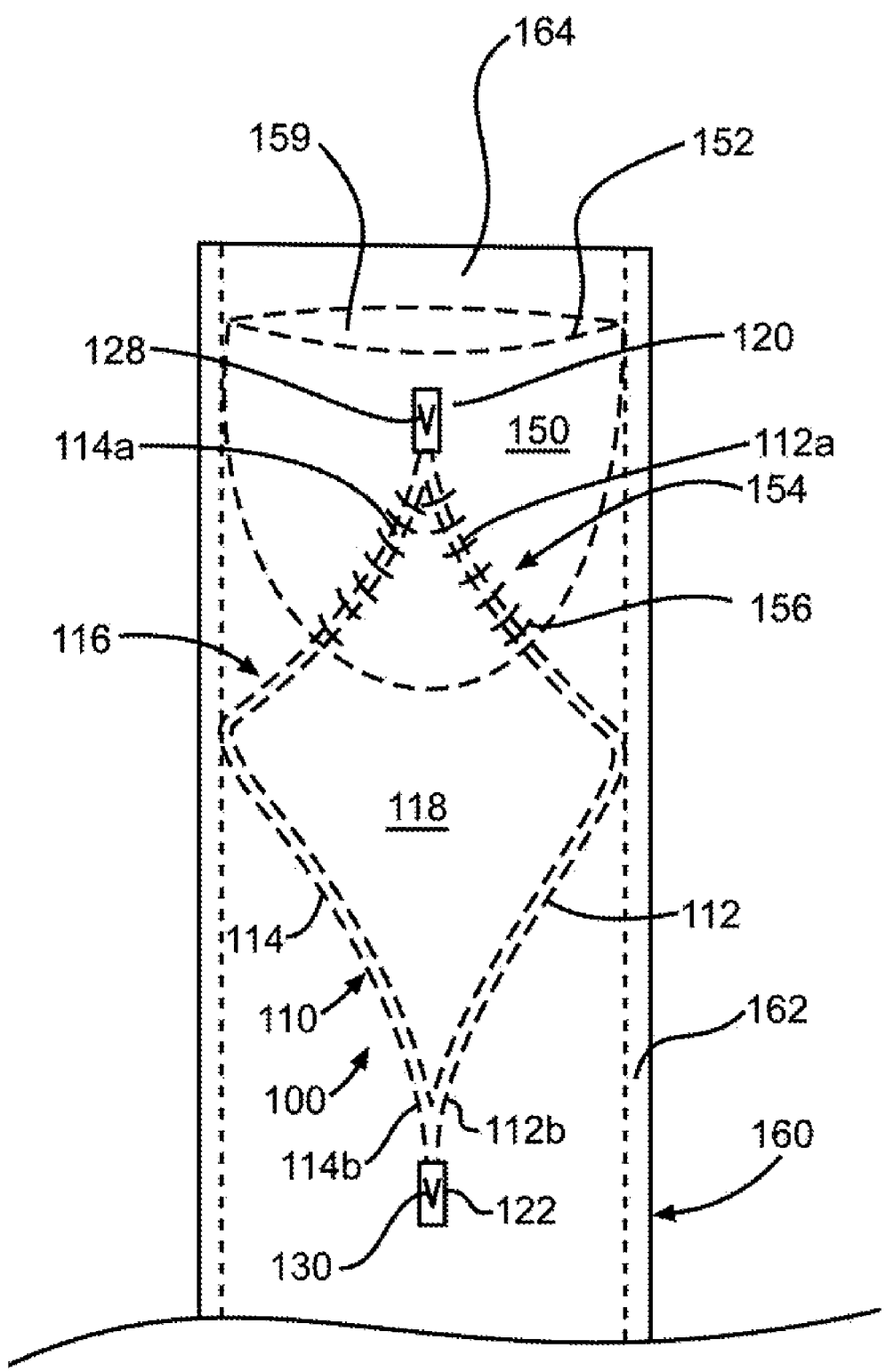
FIG. 11 is a top view of a body vessel in which an exemplary prosthetic valve has been deployed.

As illustrated in FIG. 11, two lateral portions 154, 155 of the valve member 150 are advantageously attached to the support frame by wrapping the edges of the valve member 150 around the wire members 112, 114. Also advantageously, the valve member 150 is sized and configured to extend from a point at which the wire members 112, 114 overlap and/or touch each other to the curve 112d, 114d associated with each member 112, 114. Extending the valve member 150 to this length is expected to enhance the durability of the attachment between the valve member 150 and the support frame 110 under dynamic in vivo conditions. Alternatively, the valve member 150 can be sized and configured to extend from a point at which the wire members 112, 114 overlap and/or touch each other to a point beyond the curve 112d, 114d associated with each member 112, 114.

As described in more detail below, the free edge 152 is moveable between first and second positions when the device 100 is placed within a body vessel. The valve member 150 includes slack 158 between the wire member 112, 114 that facilitates this movement of the free edge 152.

The prosthetic valve device 100 is adapted to be disposed in a body vessel 160 using percutaneous delivery techniques. The body vessel 160 can be any suitable body vessel, including any vessel of the vasculature, such as veins, arteries, and sections of the heart. Thus, the vessel 160 illustrated in the figures is illustrative only; the basic structure should not be interpreted as limiting the types of vessels in which the device can be deployed. As such, the vessel 160 includes a vessel wall 162 and defines a lumen 164 in which the valve device 100 is disposed.

Figure 12:
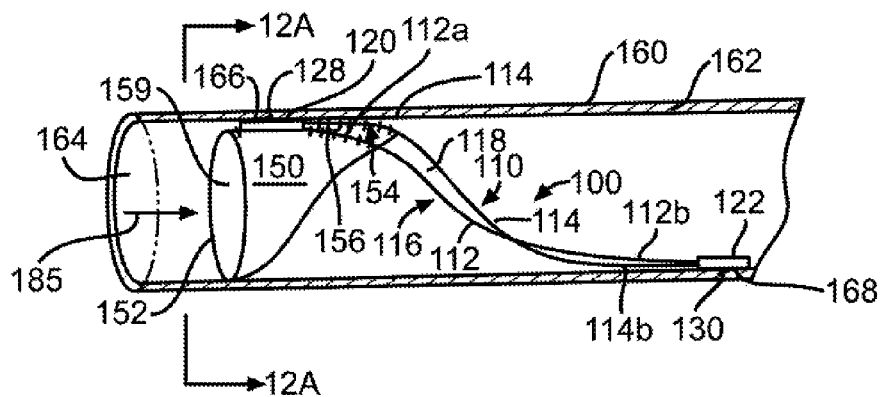
FIG. 12 is a three-quarter view of a body vessel in which the prosthetic valve illustrated in FIG. 11 has been deployed. The valve is shown in a closed configuration.
Figure 12A:
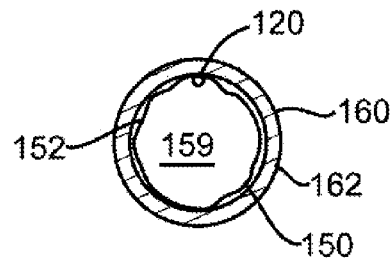
FIG. 12A is a cross sectional view of the body vessel illustrated in FIG. 12, taken along line 12A-12A.
Figure 13:
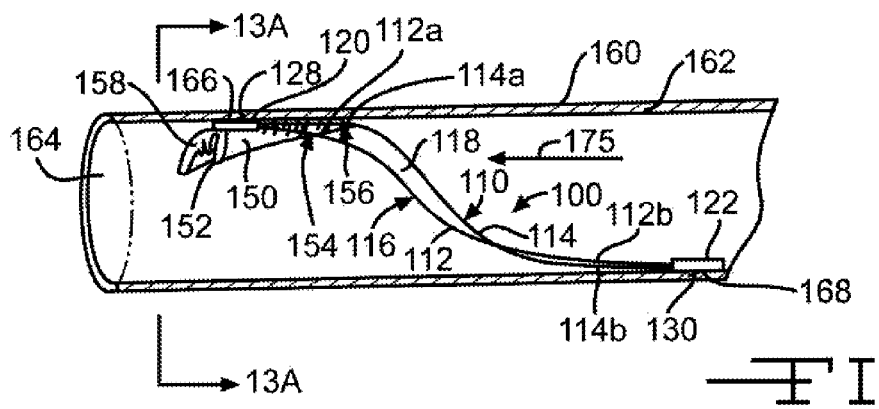
FIG. 13 is a three-quarter view of a body vessel in which the prosthetic valve illustrated in FIG. 12 has been deployed. The valve is shown in an open configuration.
Figure 13A:
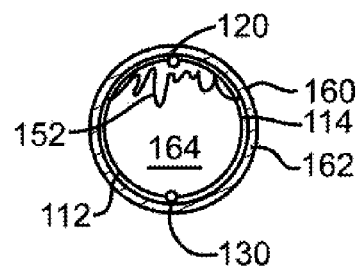
FIG. 13A is a cross sectional view of the body vessel illustrated in FIG. 13, taken along line 13A-13A.

FIGS. 12 and 12A illustrate the valve device 100 in a closed configuration while FIGS. 13 and 13A illustrate the valve device 100 in an open configuration. The valve device 100 is secured in the body vessel by the first barb 128, which passes into the vessel wall 162 at a first point 166, and the second barb 130, which passes into the vessel wall 162 at a second point 168. It is noted that the barbs 128, 130 are not necessarily drawn to scale. Indeed, microbarbs that only partially pass into the thickness of the vessel wall 162 may be used. Furthermore, a series of two or more microbarbs can be used at each barb 128, 130 location. The barbs 128, 130 are illustrated as penetrating through the entire thickness of the vessel wall only to facilitate understanding of the operation of the valve device 100 and is not required. Furthermore, a series of two or more microbarbs can be used at each barb 128, 130 location.

Also, the barbs 128, 130 can have shape memory properties of their own that facilitate anchoring of the valve device 100 in the body vessel. For example, the barbs 128, 130 can adopt an "open" configuration at room temperature and a "clamped" or "closed" configuration at another temperature, such as the expected or actual body temperature of the animal, such as a human, into which the valve device is being implanted. In the open configuration, a clearance exists between the barb and the underlying connector 120, 122 and/or wire member 112, 114. In the clamped or closed configuration, the clearance is reduced. Thus, when the transition temperature is reached, the barb 128, 130 moves closer to the connector 120, 122 and/or wire member 112, 114, which can clamp a portion of the vessel wall 162 between the barb 128, 130 and the connector 120, 122 and/or wire member 112, 114. This is expected to enhance anchoring of the valve device 100 in the body vessel 160.

As described above, the valve member 150 is moveable between first and second positions when the device 100 is placed within a body vessel 160. In the first position, illustrated in FIG. 12, the valve member 150 substantially prevents fluid flow in the direction represented by arrow 185 from flowing past the point in the body vessel 160 at which the valve device 100 is deployed. In the second position, illustrated in FIG. 13, the valve member 150 permits fluid flow in an opposite direction, represented by arrow 175, to flow through the closed cell 118 defined by the closed circumference 116. The valve member 150 moves to the first position when a pressure change and/or reversal of flow direction exerts a force on an edge or face of the valve member 150 and forces it away from the vessel wall 162 and across the lumen 164 of the vessel 160. The valve member 150 moves to the second position when a pressure change and/or reversal of flow direction exerts a force on an opposing edge or face of the valve member 150, forcing it toward vessel wall 161. The first position of the valve member 150 can be considered a closed position, and the second position can be considered an open position. By moving between these two positions, the valve member 150 provides a valving function to the medical device 100, allowing it to regulate fluid flow through the body vessel 160.

As illustrated in FIGS. 12 and 12A, the valve member forms a pocket 159 that collects fluid, substantially preventing passage through the closed cell 118 defined by the closed circumference 116 during periods of retrograde flow in which the valve member 150 is in the closed position. As best illustrated in FIGS. 13 and 13A, the valve member 150 is forced toward a portion of the vessel wall 162 (upward in the Figure) during periods of antegrade flow 175, thereby adopting the open position and allowing fluid to flow through the closed cell 118 defined by the closed circumference 116.

The medical device 100 illustrated in FIGS. 11 through 13 is a prosthetic valve, and can be used as a prosthetic venous valve. In this capacity, the device 100 is placed in a vein to regulate the flow of blood through the vein. It is believed that the valve member 150 moves to the open position, illustrated in FIG. 13, during systole in which the heart forces blood through the vein in the first direction 175. During diastole, the valve member 150 moves to the closed position, illustrated in FIG. 12, to substantially prevent fluid flow in the second, opposite direction 185. It is believed that a pressure change and reversal of flow direction occurs during the change from systole to diastole, and the valve member 150 changes position in response to these changes. Flow in the second, opposite direction 185 is commonly referred to as retrograde flow.

The valve member 150 substantially, but not entirely, prevents fluid flow in the second, opposite direction 185 for at least two reasons. First, as the valve member 150 moves from the first position to the second position, a time period passes before the valve member is in the second position, and some retrograde flow may pass through the device 100 during this time. Second, as best illustrated in FIGS. 12 and 12A, the valve member 150 does not form a complete and constant seal with the vessel wall 162 while in the second or closed position.

Figure 14:
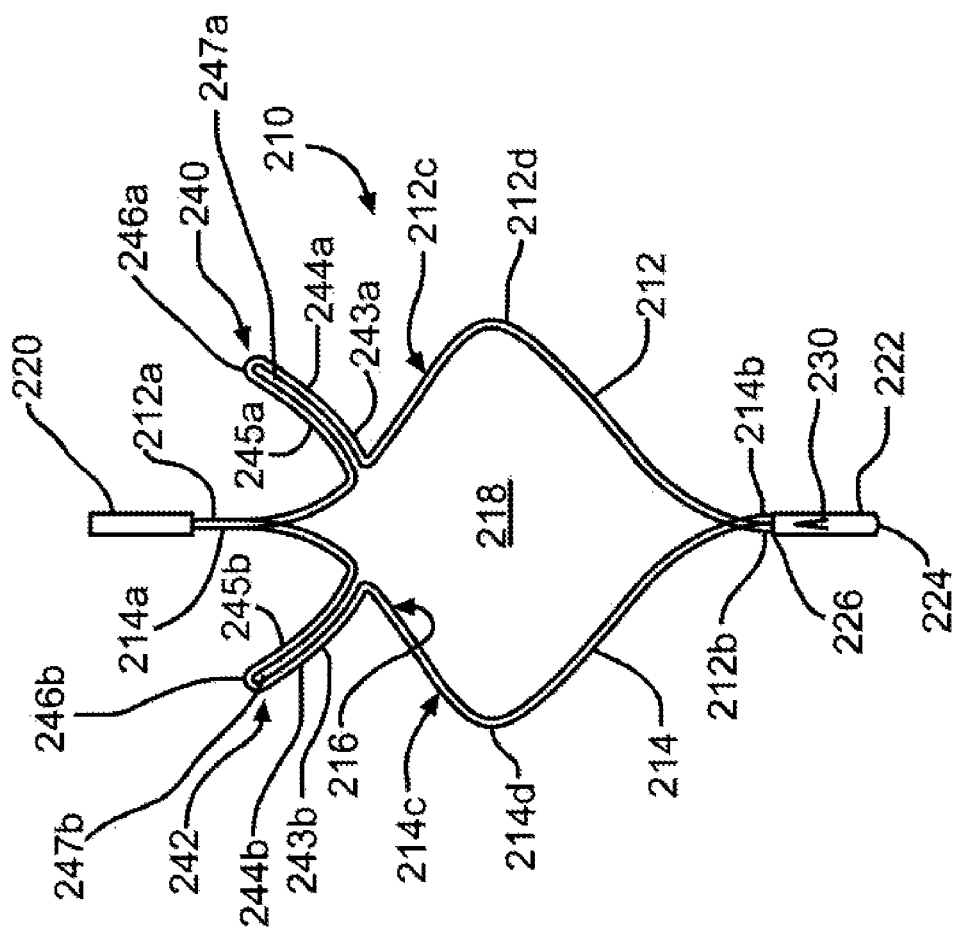
FIG. 14 is a perspective view of an exemplary support frame.

FIG. 14 illustrates a support frame 210 according another exemplary embodiment of the invention. The support frame 210 according to this embodiment is similar to the support frame 10 illustrated in FIG. 1 and described above, except as detailed below. Thus, the support frame 210 includes first 212 and second 214 wire members. The first wire member 212 includes a first end 212a and a second end 212b. The wire member 212 defines an arcuate path 212c that includes a curve 212d disposed substantially at a midpoint between the first 212a and second 212b ends. Similarly, the second wire member 214 includes first 214a and second 214b ends and defines an arcuate path 214c that includes a curve disposed substantially at a midpoint between the ends 214a, 214b. The wire members 212, 214 cooperatively define a closed circumference 216 that, in turn, defines a single closed cell 218. A first connector 220 is disposed at one end of the support frame 210 and a second connector 222 is disposed at the opposite end of the support frame 210. The first ends 212a, 214a of the first 212 and second 214 wire members are disposed within the first connector 220, and the second ends 212b, 214b of the first 212 and second 214 wire members are disposed in the second connector 222.

Each of the connectors 220, 222 is attached to the appropriate ends 212a, 212b, 214a, 214b and includes a closed 224 and an open 226 end. Pairs of the ends 212a, 212b, 214a, 214b are disposed in the open end 226 of the appropriate connector 220, 224. A first barb (not illustrated in FIG. 14) is disposed on the first connector 220 and a second barb 230 on the second connector 222, substantially opposite to the first barb. It is noted that the barbs are not necessarily drawn to scale relative to any other component and/or element of the frame 210, and are shown as relatively large elements for illustrative purposes only.

The support frame 210 according to this exemplary embodiment includes first 240 and second 242 support arms. The support arms 240, 242 provide additional surface area to the support frame 210 that can provide additional contact area between the support frame 210 and a wall of a vessel in which the frame 210 or an associated device is deployed. Furthermore, each of the support arms 240, 242 defines a loop that can be engaged by another medical device, such as a retrieval hook or other device adapted to engage one or both of the arms 240, 242, to enable repositioning and/or retrieval of the support frame 210, or a medical device that includes the support frame 210, following deployment.

Each of the support arms 240, 242 is attached to the respective wire member 212, 214. Alternatively, one or both of the support arms 240, 242 can be integrally formed by the respective wire member 212, 214.

The first support arm 240 is a closed circumference 243a defined by first 244a and second 245a lengths that extend away from the first wire member 212 and a curve 246a disposed between the first 244a and second 245b lengths. The closed circumference 243a defines an opening 247a between the first 244a and second 245a lengths and the curve 246a.

The second support arm 242 is a closed circumference 243b defined by first 244b and second 245b lengths that extend away from the second wire member 214 and a curve 246b disposed between the first 244b and second 245b lengths. The closed circumference 243b defines an opening 247b between the first 244b and second 245b lengths and the curve 246b.

Figure 15:
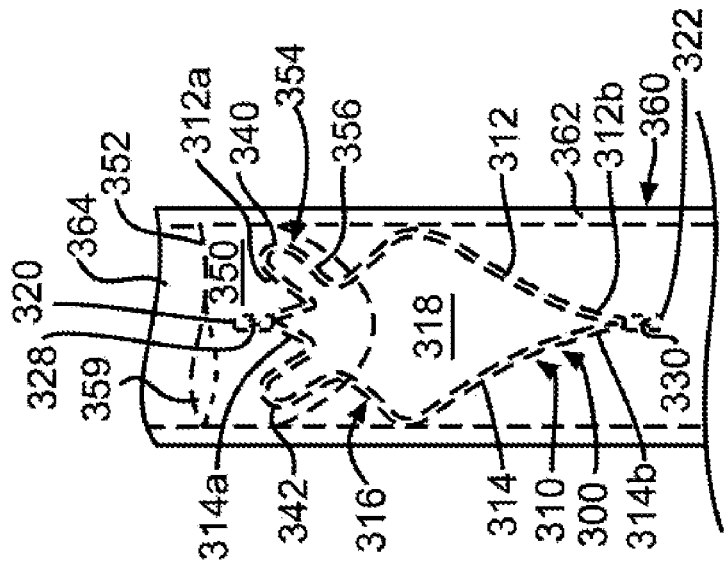
FIG. 15 is a top view of a body vessel in which an exemplary prosthetic valve has been deployed.

FIGS. 15 through 17 illustrate a valve device 300 according to another exemplary embodiment of the invention. The valve device 300 of this embodiment is similar to the valve device 100 illustrated in FIG. 11 and described above, except as detailed below. In each of the figures, the valve device is disposed within a body vessel 360. The body vessel 360 has a wall 362 and defines a lumen 364.

The valve device 300 according to this embodiment includes a support frame 310 similar to the support frame 210 illustrated in FIG. 14 and described above, and an attached valve member 350. The support frame 310 includes first 312 and second 314 wire members. The first wire member 312 includes a first end 312a and a second end 312b. The wire member 312 defines an arcuate path 312c that includes a curve 312d disposed substantially at a midpoint between the first 312a and second 312b ends. Similarly, the second wire member 314 includes first 314a and second 314b ends and defines an arcuate path 314c that includes a curve disposed substantially at a midpoint between the ends 314a, 314b. The wire members 312, 314 cooperatively define a closed circumference 316 that, in turn, defines a single closed cell 318. A first connector 320 is disposed at one end of the support frame 310 and a second connector 322 is disposed at the opposite end of the support frame 310. The first ends 312a, 314a of the first 312 and second 314 wire members are disposed within the first connector 320, and the second ends 312b, 314b of the first 312 and second 314 wire members are disposed in the second connector 322.

Each of the connectors 320, 322 is attached to the appropriate ends 312a, 312b, 314a, 314b and includes a closed 324 and an open 326 end. Pairs of the ends 312a, 312b, 314a, 314b are disposed in the open end 326 of the appropriate connector 320, 324. A first barb (not illustrated in FIG. 15) is disposed on the first connector 320 and a second barb 330 on the second connector 322, substantially opposite to the first barb. It is noted that the barbs are not necessarily drawn to scale relative to any other component and/or element of the frame 310, and are shown as relatively large elements for illustrative purposes only.

The support frame 310 includes first 340 and second 342 support arms attached to or formed by the respective wire member 312, 314. The first support arm 340 is a closed circumference 343a defined by first 344a and second 345a lengths that extend away from the first wire member 312 and a curve 346a disposed between the first 344a and second 345b lengths. The closed circumference 343a defines an opening 347a between the first 344a and second 345a lengths and the curve 346a.

The second support arm 342 is a closed circumference 343b defined by first 344b and second 345b lengths that extend away from the second wire member 314 and a curve 346b disposed between the first 344b and second 345b lengths. The closed circumference 343b defines an opening 347b between the first 344b and second 345b lengths and the curve 346b.

The valve member 350 includes a free edge 352 that is not attached to the support frame 310 and at least one portion 354 that is attached to the support frame 310 in any suitable manner, such as sutures 356. Preferably, as illustrated in the figures, the valve member 350 is attached to the support frame along attachment pathways defined by the first 340 and second 342 support arms. The free edge 352 is moveable between first and second positions when the device 300 is placed within a body vessel. The valve member 350 can include slack between the wire member 312, 314 that facilitates this movement of the free edge 352.

The prosthetic valve device 300 is adapted to be disposed in a body vessel 360 using percutaneous delivery techniques. The vessel 360 includes a vessel wall 362 and defines a lumen 364 in which the valve device 300 is disposed. FIG. 16 illustrates the valve device 300 in a closed configuration and FIG. 17 illustrates the valve device 300 in an open configuration.

The valve device 300 is secured in the body vessel 360 by the first barb 328, which passes through the vessel wall 362 at a first point 366, and the second barb 330, which passes through the vessel wall 362 at a second point 368.

The valve member 350 moves between the first and second positions similar to the manner in which the valve member 150 illustrated in FIGS. 12 and 13 does so. In this embodiment, though, the support arms 340, 342 limit the movement the valve member can make toward the vessel wall when the valve member 350 moves to the second position. Furthermore, the support arms 340, 342 provide support to the valve pocket when the valve member 350 is in the open position, which is expected to aid in prevention eversion of and/or damage to the valve member 350.

FIG. 20 illustrates an occluder 400 according to an embodiment of the invention. The occluder 400 includes a support frame 410 according to an embodiment of the invention and a graft member 490 attached to the support frame 410.

The support frame 410 is similar to the support frame 10 illustrated in FIG. 1 and described above. Thus, the support frame 410 includes first 412 and second 414 wire members. The first wire member 412 includes a first end 412a and a second end 412b. The wire member 412 defines an arcuate path 412c that includes a curve 412d disposed substantially at a midpoint between the first 412a and second 412b ends. Similarly, the second wire member 414 includes first 414a and second 414b ends and defines an arcuate path 414c that includes a curve 414d disposed substantially at a midpoint between the ends 414a, 414b. The wire members 412, 414 cooperatively define a closed circumference 416 that, in turn, defines a single closed cell 418. A first connector 420 is disposed at one end of the support frame 410 and a second connector 422 is disposed at the opposite end of the support frame 410. The first ends 412a, 414a of the first 412 and second 414 wire members are disposed within the first connector 420, and the second ends 412b, 414b of the first 412 and second 414 wire members are disposed in the second connector 422.

Each of the connectors 420, 422 is attached to the appropriate ends 412a, 412b, 414a, 414b and includes a closed 424 and an open 426 end. Pairs of the ends 412a, 412b, 414a, 414b are disposed in the open end 426 of the appropriate connector 420, 424. A first barb (not illustrated in FIG. 20) is disposed on the first connector 420 and a second barb 430 on the second connector 422, substantially opposite to the first barb. It is noted that the barbs are not necessarily drawn to scale relative to any other component and/or element of the frame 410, and are shown as relatively large elements for illustrative purposes only.

The graft member 490 is similar in construction to the valve member described in the various valve device embodiments described above, except that the graft member 490 is attached to the support frame 410 in a manner that substantially closes the open cell 418 defined by the closed circumference 416. Thus, the edge 492 of the graft member 490 is attached to the support frame 410 around substantially the entire closed circumference 416. Similar to the valve embodiment, sutures 494 or other suitable means for attaching a graft member to a support frame can be used to form the desired attachment.

As a result of the closing of the open cell 418, the occluder 400, when deployed in a body vessel, can substantially block fluid flow through the body vessel at the point of deployment. This effect may be desirable in various clinical situations, including the treatment of tumors, arteriovenous malformations (AVM's), and other situations in which it is desirable to block the flow of blood or other fluid to a particular site.

FIGS. 18 and 19 illustrate another exemplary valve device 500. The valve device 500 of this embodiment is similar to the valve device 300 illustrated in FIGS. 15 through 17 and described above, except as detailed below.

The valve device 500 according to this embodiment includes a support frame 510 and an attached bioprosthetic valve 550. The support frame 510 includes first 512 and second 514 wire members. The first wire member 512 includes a first end 512a and a second end 512b. The wire member 512 defines an arcuate path that includes a curve disposed substantially at a midpoint between the first 512a and second 512b ends. Similarly, the second wire member 514 includes first 514a and second 514b ends and defines an arcuate path that includes a curve disposed substantially at a midpoint between the ends 514a, 514b. The wire members 512, 514 cooperatively define a closed circumference 516 that, in turn, defines a single closed cell 518.

The wire members 512, 514 of the support frame 510 comprise a unitary structure that has been cut from a tube, such as from a nitinol tube. Thus, the support frame 510 lacks the connectors described above and, instead, the wire members 512, 514 simply meet and join at their respective ends. A first plurality of barbs 528 is disposed at a first end of the support frame 510, and a second plurality of barbs 530 is disposed at a second end of the support frame. As illustrated in the Figure, the each barb of the plurality of barbs 528, 530 is advantageously adapted to pass into a partial thickness of a wall 562 of a body vessel 560 in which the valve device 500 is deployed.

The support frame 510 includes first 540 and second 542 support arms defined by the respective wire member 512, 514. In this embodiment, each of the support arms 540, 542 is an open curve that defines a partial, elongated loop in the respective wire member 512, 514 of the support frame 510.

The bioprosthetic valve can comprise any suitable bioprosthetic valve, and the specific bioprosthetic valve selected for a valve device according to a particular embodiment will depend on various considerations, including the body vessel into which the valve device is intended to be implanted. Examples of suitable bioprosthetic valves include those describe in U.S. Provisional Application Ser. No. 60/980,770, which is hereby incorporated into this disclosure in its entirety. The bioprosthetic valve 550 is similar to the bioprosthetic valves described therein, and will be described herein only briefly. The bioprosthetic valve 550 includes a patch 552 of tissue connected to a single leaflet 554. The leaflet 554 has a free edge 556 that moves in response to differing pressures in the body vessel 560, or other suitable environmental changes, to open and close the valve device 500 and to selectively permit antegrade fluid flow, represented by arrow 575 in FIG. 13, and substantially prevent retrograde fluid flow, represented by arrow 585 in FIG. 14, through the body vessel 560.

While tissue valves and sheet form valve members can be used with the support frames according to the disclosure, the support frame 510 illustrated in FIGS. 18 and 19 is particularly well-suited for use with single leaflet bioprosthetic valves, such as the bioprosthetic valve 550 illustrated in FIGS. 18 and 19, at least because of the curvilinear attachment pathway provided by the arms 540, 542, which provides a pocket definition function believed to be critical for the formation of a functional valve from a single leaflet-containing bioprosthetic valve.

The bioprosthetic valve 550 is attached to one end of the support frame 510, using sutures or any other suitable means for attaching tissue to a support frame. The leaflet 554 is advantageously attached to the wire members 512, 514 along an attachment pathway that extends along substantially the entire length of the open curve defined by the arms 540, 542, although shorter and longer attachment pathways can be used. As illustrated in FIGS. 18 and 19, this produces a curvilinear attachment pathway 570. Also as illustrated in FIGS. 18 and 19, it is considered particularly advantageous for the attachment pathway to include the apex 572 of the curves defined by the arms 540, 542, as this is expected to increase the overall ruggedness of the attachment between the leaflet 554 and the frame 510 in the dynamic environment of a body vessel 560. Examples of other suitable means for attaching a tissue valve and/or a tissue to a support frame include clips, staples, adhesives, and tissue welding materials and techniques. As best illustrated in FIG. 19, the free edge 556 of the leaflet 554 is substantially free of the support frame 510 and extends between the arms 540, 542, allowing the free edge 556 to move within the confines of the wire members 512, 514 to effect opening and closing of the valve device 500.

Any suitable tissue can be used to form a bioprosthetic valve for use in a valve device according to an embodiment of the invention. The tissue selected for a bioprosthetic valve in a device according to a particular embodiment of the invention need only be capable of being attached to the support frame in a manner that forms the desired valve configuration. The tissue should be selected to provide desirable behavior of the valve following deployment of the biomedical valve device in a body vessel. Examples of suitable tissues include pleura, such as a lining from the peritoneal cavity, a tissue capsule, such as a renal capsule, and a vessel wall or portion thereof. The use of tissues other than vessel walls might be particularly advantageous when fashioning a biomedical valve device according to an embodiment of the invention that is intended to be implanted in a patient that is missing a particular body vessel or has a damaged portion of a particular body vessel. For example, in humans that have already lost a greater saphenous or other donor vessel, use of a renal capsule or other tissue might be advantageous.

FIG. 18 illustrates the valve device 500 in a closed configuration, in which the leaflet 554 has substantially opened to define a valve pocket 558 between the leaflet 554 and patch 552 that substantially prevents retrograde fluid flow, represented by arrow 585, from passing through the body vessel 560. The leaflet free edge 556 has been forced outwardly by retrograde fluid flow 585, substantially forcing the free edge 556 away from the patch 552 and allowing the valve pocket 558 to open. Over time, the valve pocket 558 fills with fluid until antegrade fluid flow or other forces, such as a change in the pressure differential across the valve device 500, favors a transition to the open configuration, as illustrated in FIG. 18 and described above.

FIG. 19 illustrates the valve device 500 in an open configuration, in which the free edge 556 of the leaflet 554 has been forced inward by antegrade fluid flow 575, which substantially forces portions of the leaflet 554 toward the patch 552. The free edge 556 folds upon itself and/or other portions of the leaflet 554 when the valve device 500 is in this configuration, substantially reducing the volume of the valve pocket 558 defined by the leaflet 554 and patch 552. In addition to the folding action of the leaflet, an elastic transition may take place prior to, during, and/or after the leaflet folds inward. With a bioprosthetic valve, it is believed that the leaflet elastically contracts to a certain point, and subsequently folds inward. When the valve device transitions to the open configuration from a closed configuration, described below with reference to FIG. 19, fluid is substantially forced out of the valve pocket 558, effectively flushing the valve device 500.

A comparison of the valve device 500 illustrated in FIGS. 18 and 19 to the valve device 300 illustrated in FIGS. 16 and 17 illustrates different functions for the support arms in the two devices. In valve device 300, arms 340, 342 effectively provide a backstop for the valve member 350 as it moves to the closed configuration, which may assist in the prevention of prolapse of the valve device 300. In valve device 500, the arms 540, 542 include the additional function of assisting in the defining of the valve pocket 558. As illustrated in FIGS. 18 and 19, the arms 540, 542 define the lateral boundaries of the valve pocket 558 in both the open and closed configurations.

FIG. 21 illustrates a support device 600 according to an exemplary embodiment of the invention. The support device 600 comprises a support frame 610 that includes first 610a and second 610b frame portions. Each frame portion 610a, 610b is similar to the support frame 10 illustrated in FIG. 1 and described above. Thus, the first frame portion 610a includes first 612a and second 612b wire members connected to each other at opposing ends with connectors 620a, 620b. Similarly, the second frame portion 612b includes first 614a and second 614b wire members connected to each other at opposing ends with connectors 622a, 622b.

The first wire member 612a of the first frame portion 610a and the first wire member 614a of the second frame portion 610b intersect at intersection 616a. Similarly, the second wire member 612b of the first frame portion 610a and the second wire member 614b of the second frame portion 610b intersect at intersection 616b. The intersections 616a, 616b can be a simple crossing of wire members, with optional contact between the members, or can comprise a mechanical connection between the members formed using any suitable means for connecting portions of support frame to each other, including rivets, welds, post and hole connections, and other suitable structures. A connection that allows the relevant wire members to move relative to each other at the intersection 616a, 616b is considered advantageous at least because it is expected to allow the support device 600 to flex in response to movement of a the wall 662 of a body vessel 660 in which the device is implanted.

The support device 600 can be used as a stent to provide intraluminal support to a body vessel. Alternatively, as described more fully below, the support device 600 can be used in a valve device or other suitable medical device.

FIG. 22 illustrates a valve device 700 according to an exemplary embodiment of the invention. The valve device 700 includes a support frame 710 and an attached bioprosthetic valve 750. The valve 750 opens and closes to regulate fluid flow through a body vessel 760 in which the device 700 is implanted.

The support frame 710 is similar to the support frame 610 illustrated in FIG. 12 and described above. Thus, the support frame 710 includes first 710a and second 710b frame portions. The first frame portion 710a includes first 712a and second 712b wire members connected to each other at opposing ends with connectors 720a, 720b. Similarly, the second frame portion 712b includes first 714a and second 714b wire members connected to each other at opposing ends with connectors 722a, 722b.

The first wire member 712a of the first frame portion 710a and the first wire member 714a of the second frame portion 710b intersect at intersection 716a. Similarly, the second wire member 712b of the first frame portion 710a and the second wire member 714b of the second frame portion 710b intersect at intersection 716b.

The bioprosthetic valve 750 includes a patch 752 of tissue connected to a single leaflet 754. The leaflet 754 has a free edge 756 that moves in response to differing pressures in the body vessel 760, or other suitable environmental changes, to regulate fluid flow through the body vessel 760.

The bioprosthetic valve 750 is attached to the support frame 710 at one end of the support frame 710, using sutures or any other suitable means for attaching tissue to a support frame. The leaflet 754 is substantially free of the support frame 710, allowing the free edge 756 to move within the confines of the wire members 712, 714.

As described above with reference to FIGS. 11 through 13 and 15 through 17, support frames according to the disclosure provide a suitable frame onto which a simple valve member, such as a sheet of material, can be attached to form a functional prosthetic valve. Also, as described above with reference to FIGS. 18 and 19, support frames according to the disclosure provide a suitable frame onto which more complex valve members, such as a natural valve harvested from an animal or human, can be attached to form a functional prosthetic valve device. Furthermore, as illustrated in FIG. 20 and described above, the support frames according to the disclosure can be used in other types of medical devices as well, such as occluders. As such, the support frames according to the disclosure provide a relatively simple platform onto which a variety of valve members and other additional elements can be attached to form a wide array of useful medical devices.

While various embodiments are described with reference to specific features of particular drawings, it is understood that the various elements and/or features described herein in connection with one particular embodiment can be combined with those of another without departing from the scope of the invention. For example, the arms 340, 342 of the support frame illustrated in FIG. 15 could be incorporated into the support frame 410 of the occluder device 400 illustrated in FIG. 20.

The embodiments described and illustrated herein provide examples of the invention, and are not intended to limit the scope of the invention in any manner. Rather, they serve only to aid those skilled in the art to make and use the invention.

What is claimed is:

1. A low profile support frame for intraluminal medical devices, said support frame having a lengthwise axis, a radially compressed configuration and a radially expanded configuration, said low profile support frame comprising:
   a first wire member having first and second ends and defining a first arcuate path with a first curve disposed between the first and second ends, the first arcuate path comprising only a single sigmoidal curve;
   a second wire member having third and fourth ends and defining a second arcuate path with a second curve disposed between the third and fourth ends, the second arcuate path comprising only a single sigmoidal curve;
   a first connector connecting the first and third ends; and
   a second connector connecting the second and fourth ends and spaced from the first connector on said lengthwise axis of said support frame;
   wherein substantially no portion of said support frame is disposed on a first transverse axis of said support frame opposite the first and third ends and substantially no portion of said support frame is disposed on a second transverse axis of said support frame opposite the second and fourth ends when said support frame is in said radially expanded configuration;
   wherein the first and third ends extend along a third axis and the second and fourth ends extend along a fourth axis different from the third axis; and
   wherein the third axis and the fourth axis are substantially parallel to the lengthwise axis.

2. The low profile support frame of claim 1, wherein the first connector comprises a separate member attached to the first and third ends.

3. The low profile support frame of claim 2, wherein the second connector comprises a separate member attached to the second and fourth ends.

4. The low profile support frame of claim 1, wherein the first and second wire members comprise struts and at least one of the connectors comprises a joint that is continuously formed with the first and second wire members.

5. The low profile support frame of claim 1, further comprising at least one barb disposed on the first connector.

6. The low profile support frame of claim 1, further comprising a first barb disposed on the first connector and a second barb disposed on the second connector.

7. The low profile support frame of claim 6, wherein the first barb extends away from the first connector in a first direction and the second barb extends away from the second connector in a second, different direction.

8. The low profile support frame of claim 1, wherein the first end is disposed on top of the third end with respect to a plane containing the closed circumference when said support frame is in a compressed configuration and wherein the second and fourth ends are disposed substantially side-by-side with respect to the plane.

9. The low profile support frame of claim 1, wherein the first curve is disposed substantially opposite the second curve.

10. The low profile support frame of claim 1, further comprising first and second support arms, the first support arm attached to the first wire member and comprising first and second lengths extending away from the first wire member and a third curve disposed between the first and second lengths, and the second support arm attached to the second wire member and comprising third and fourth lengths extending away from the second wire member and a fourth curve disposed between the third and fourth lengths.

11. The low profile support frame of claim 10, wherein the first support arm at least partially defines a closed circumference providing an opening between the first length, the second length, and the third curve.

12. The low profile support frame of claim 11, wherein the second support arm at least partially defines a closed circumference providing a second opening between the third length, the fourth length, and the fourth curve.

13. The low profile support frame of claim 1, wherein the first and second wire members are formed of nitinol.

14. A low profile support frame for intraluminal medical devices, said support frame having a lengthwise axis, a radially compressed configuration and a radially expanded configuration, said low profile support frame comprising:
   a first strut defining a first arcuate path and having first and second ends, the first arcuate path comprising only a single sigmoidal curve;
   a second strut defining a second arcuate path and having third and fourth ends, the second arcuate path comprising only a single sigmoidal curve;
   a first connector continuously formed with and connecting the first and third ends; and
   a second connector continuously formed with and connecting the second and fourth ends;
   wherein substantially no portion of said support frame is disposed on a first transverse axis of said support frame opposite the first and third ends and substantially no portion of said support frame is disposed on a second transverse axis of said support frame opposite the second and fourth ends when said support frame is in said radially expanded configuration;

wherein the first and third ends extend along a third axis and the second and fourth ends extend along a fourth axis different from the third axis; and wherein the third axis and the fourth axis are substantially parallel to the lengthwise axis.

15. The low profile support frame of claim 14, further comprising at least one barb disposed on the first connector.

16. The low profile support frame of claim 14, further comprising a first barb disposed on the first connector and a second barb disposed on the second connector.

17. The low profile support frame of claim 16, wherein the first barb extends away from the first connector in a first direction and the second barb extends away from the second connector in a second, different direction.

18. The low profile support frame of claim 14, wherein the first and second struts and first and second connectors cooperatively define a closed circumference defining a closed cell.

19. The low profile support frame of claim 14, wherein said support frame is formed of nitinol.

20. A low profile support frame for intraluminal medical devices, said support frame having a lengthwise axis, a radially compressed configuration and a radially expanded configuration, said low profile support frame comprising:

a first wire member having first and second ends and defining a first arcuate path with a first curve disposed between the first and second ends, the first arcuate path comprising only a single sigmoidal curve;

a second wire member having third and fourth ends and defining a second arcuate path with a second curve disposed between the third and fourth ends, the second arcuate path comprising only a single sigmoidal curve;

a first connector circumferentially disposed around and connecting the first and third ends; and a second connector circumferentially disposed around and connecting the second and fourth ends, the second connector spaced from the first connector on said lengthwise axis of said support frame;

wherein substantially no portion of said support frame is disposed on a first transverse axis of said support frame opposite the first and third ends and substantially no portion of said support frame is disposed on a second transverse axis of said support frame opposite the second and fourth ends when said support frame is in said radially expanded configuration;

wherein the first and third ends extend along a third axis and the second and fourth ends extend along a fourth axis different from the third axis; and wherein the third axis and the fourth axis are substantially parallel to the lengthwise axis.

21. A low profile medical device, said medical device having a lengthwise axis, a radially compressed configuration and a radially expanded configuration, said low profile medical device consisting of:

a first wire member having first and second ends and defining a first arcuate path with a first curve disposed between the first and second ends;

a second wire member having third and fourth ends and defining a second arcuate path with a second curve disposed between the third and fourth ends;

a first connector connecting the first and third ends; and a second connector connecting the second and fourth ends and spaced from the first connector on said lengthwise axis of said medical device;

wherein substantially no portion of said medical device is disposed on a first transverse axis of said medical device opposite the first and third ends and substantially no portion of said medical device is disposed on a second transverse axis of said medical device opposite the second and fourth ends when said medical device is in said radially expanded configuration;

wherein the first and third ends extend along a third axis and the second and fourth ends extend along a fourth axis different from the third axis; and wherein the third axis and the fourth axis are substantially parallel to the lengthwise axis.

* * * * *